(12) United States Patent
Haefner et al.

(10) Patent No.: US 6,169,918 B1
(45) Date of Patent: Jan. 2, 2001

(54) CARDIAC RHYTHM MANAGEMENT SYSTEM WITH CROSS-CHAMBER SOFT BLANKING

(75) Inventors: Paul A. Haefner, Circle Pines; Gary Thomas Seim, Minneapolis, both of MN (US)

(73) Assignee: Cardiac Pacemakers, Inc., St. Paul, MN (US)

(*) Notice: Under 35 U.S.C. 154(b), the term of this patent shall be extended for 0 days.

(21) Appl. No.: 09/181,482

(22) Filed: Oct. 28, 1998

(51) Int. Cl.$^7$ ........................................... A61B 5/04
(52) U.S. Cl. ...................... 600/509; 607/9; 128/901
(58) Field of Search ................ 607/4, 5, 9; 600/509, 600/510, 521; 128/901, 902

(56) References Cited

U.S. PATENT DOCUMENTS

| | | |
|---|---|---|
| 5,339,820 | 8/1994 | Henry et al. ........................... 128/696 |
| 5,620,466 | 4/1997 | Haefner et al. . |
| 5,658,317 | 8/1997 | Haefner et al. . |
| 5,662,688 | 9/1997 | Haefner et al. . |
| 5,690,683 | 11/1997 | Haefner et al. . |
| 5,709,215 | * 1/1998 | Perttu et al. .......................... 600/521 |
| 5,755,738 | 5/1998 | Kim et al. ................................ 607/9 |
| 5,755,739 | 5/1998 | Sun et al. ............................... 607/14 |

* cited by examiner

Primary Examiner—George R. Evanisko
(74) Attorney, Agent, or Firm—Schwegman, Lundberg, Woessner & Kluth, P.A.

(57) ABSTRACT

A cardiac rhythm management system provides cross-chamber "soft blanking." It senses desired electrical heart activity signals associated with a first chamber electrode while reducing unwanted signals (paces and depolarizations) associated with a second chamber of the heart. Detection of a cross-chamber event associated with the second chamber increase a time-varying first chamber sensing threshold, but does not result in completely ignoring signals associated with the first chamber for an appreciable amount of time. As a result, actual first chamber events are less likely to escape detection, such that critically important therapy is properly delivered to the patient.

40 Claims, 12 Drawing Sheets

CARDIAC RHYTHM MANAGEMENT SYSTEM WITH CROSS-CHAMBER SOFT BLANKING

FIELD OF THE INVENTION

This invention relates generally to cardiac rhythm management systems and particularly, but not by way of limitation, to a cardiac rhythm management system with cross-chamber "soft blanking" for sensing desired signals and reducing unwanted noise.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias is via drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, or pacers. Pacers deliver timed sequences of low energy electrical stimuli, called pace pulses, to the heart. Heart contractions are initiated in response to such pace pulses. By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a countershock. The countershock interrupts the tachyarrhythmia, allowing the heart to reestablish a normal rhythm for the efficient pumping of blood. In addition to pacers, cardioverters, and defibrillators, cardiac rhythm management systems also include, among other things, pacer/defibrillators that combine the functions of pacers and defibrillators, drug delivery devices, and any other systems or devices for diagnosing or treating cardiac arrhythmias.

Modern cardiac rhythm management systems are also typically capable of sensing intrinsic electrical heart activity signals. These electrical heart activity signals include cardiac depolarizations that are autonomously produced by the heart. The depolarizations initiate the contractions of the muscle tissue of the heart. These contractions, in turn, pump blood through the circulatory system.

One example of a cardiac rhythm management system that senses intrinsic electrical heart activity signals would be a dual-chamber implantable pacer (or pacer/defibrillator) that includes a pulse generator implanted subcutaneously, such as in the abdomen or in the pectoral region of the patient's upper chest near the clavicle bone. The pulse generator includes a power source, such as a battery, as well as sensing, therapy, and timing circuits. The pulse generator is coupled to the heart via endocardial leadwires. Such leadwires are typically routed from the pulse generator to the heart through blood vessels. Electrodes are located at the terminal end of these leadwires, distal from the pulse generator. The electrodes are typically positioned in the right atrium and right ventricle of the heart. Pacing pulses are delivered to the heart via the electrodes. Moreover, the intrinsic electrical heart activity signals are received at the electrodes and communicated to the pulse generator via the leadwires. At the pulse generator, atrial and ventricular sensing circuits detect atrial and ventricular depolarizations in the respective atrial and ventricular electrical heart activity signals. The pulse generator adjusts the therapy delivered according to the sensed atrial and ventricular depolarization information. In one mode of operation, for example, the pulse generator withholds delivery of a scheduled pacing pulse when it detects that the heart is already contracting as the result of an intrinsic cardiac depolarization.

Sensing intrinsic heart activity signals in each of the atrium and ventricle is complicated by the fact that an electrode placed in one chamber may receive not only intrinsic heart activity signals from that chamber of the heart, but the electrode may also receive unwanted "cross-chamber" intrinsic heart activity signals, that is, far-field noise signals resulting from depolarizations in the other chamber of the heart. For example, this is particularly problematic in using the atrial electrode to detect atrial depolarizations. Because ventricular depolarizations typically have a larger signal amplitude than atrial depolarizations, the atrial electrode is likely to detect the ventricular depolarization as well as the atrial depolarization.

At least two problems are caused by cross-chamber sensing of heart activity signals originating in a heart chamber other than that in which the electrode is located. First, in the above example, the pulse generator may erroneously recognize the cross-chamber ventricular depolarization as being an atrial depolarization. As a result, the pulse generator may improperly withhold delivery of a pace pulse to the atrium because it erroneously thought the atrium was already contracting. Second, the occurrence of ventricular depolarization may obscure detection of an atrial depolarization that occurs at about the same time as the ventricular depolarization. Thus, cross-chamber sensing of a ventricular depolarization by the atrial electrode results in a noisy signal at the atrial electrode that makes it more difficult for the atrial sensing circuit to detect an actual atrial depolarization. Conversely, cross-chamber sensing of an atrial depolarization by the ventricular electrode makes it more difficult for the ventricular sensing circuit to detect an actual ventricular depolarization.

Cross-chamber noise problems have been described above with respect to sensed intrinsic cross-chamber heart activity signals. However, the delivery of a pacing pulse to the heart by the pulse generator also causes similar noise problems, making intrinsic heart activity signals difficult to detect, both in the chamber of the heart to which the pace pulse was delivered, as well as at the electrode located in the opposite chamber of the heart.

One technique for dealing with cross-chamber sensing of unwanted far-field signals is referred to as cross-chamber blanking. In one example of this technique, the occurrence of a ventricular event (i.e., a sensed ventricular depolarization or a delivered ventricular pace pulse) triggers a lengthy time period, referred to as a blanking or refractory period. During the blanking period, electrical heart activity signals received at the atrial electrode are simply ignored. In this way, the atrial sensing circuit isn't confused by unwanted cross-chamber electrical signals resulting from ventricular depolarizations or paces. Similarly, the occurrence of an atrial event (i.e., a sensed atrial depolarization or a delivered atrial pace pulse) triggers a blanking period during which time the electrical heart activity signals received at the ventricular electrode are ignored. In this way, the ventricular sensing circuit isn't confused by unwanted cross-chamber signals resulting from atrial depolarizations or paces.

One limitation of the above-described cross-chamber blanking technique is that it requires the use of relatively long blanking periods. For example, it is not uncommon to ignore signals at the atrial electrode for a blanking period of approximately between 80–90 milliseconds after the occurrence of a ventricular event. However, in patients having cardiac arrhythmias, and particularly patients with tachyarrhythmias, it is quite common to lose synchronization between atrial and ventricular depolarizations. For example, an actual atrial depolarization may occur during the 80–90 millisecond blanking period that follows a ventricular event. However, such an atrial depolarization would be improperly ignored according to the cross-chamber blanking technique described above. As a result of the missed atrial depolarization, the pulse generator may improperly issue a pace pulse to the atrium. In such a case, because the pace pulse is not delivered at the proper time, the pulse generator may operate to decrease the pumping efficiency of the heart. One possible result is that a cardiac arrhythmia could be initiated by multiple occurrences of improperly timed pace pulses. Another possible result is that the detection of a cardiac arrhythmia could be delayed by multiple occurrences of atrial depolarizations during blanking periods. Moreover, although the above example describes the improper delivery of atrial paces due to cross-chamber sensing of electrical signals from the ventricle, it is understood that ventricular therapy may also be adversely affected by cross-chamber sensing of electrical signals from the atrium. Thus, there is a need for techniques that more effectively mitigate the problem of cross-chamber sensing of far-field electrical signals.

SUMMARY

The present cardiac rhythm management system provides, among other things, cross-chamber "soft blanking." The system allows sensing of desired electrical heart activity signals from an electrode located in a first chamber of the heart, while reducing unwanted noise signals originating in a second chamber of the heart. Such unwanted noise signals include, among other things, intrinsic cardiac depolarizations associated with the second chamber of the heart as well as pace pulses delivered to the second chamber of the heart. The soft-blanking advantageously minimizes the erroneous sensing of second-chamber depolarizations as first-chamber depolarizations, which could result in a pace pulse being inappropriately withheld from the first chamber when it should have been delivered. Moreover, because the detection of a cross-chamber event in the second chamber does not result in completely ignoring signals in the first chamber for an appreciable amount of time, actual first chamber events are less likely to escape detection. Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views.

DETAILED DESCRIPTION

Figure 1:
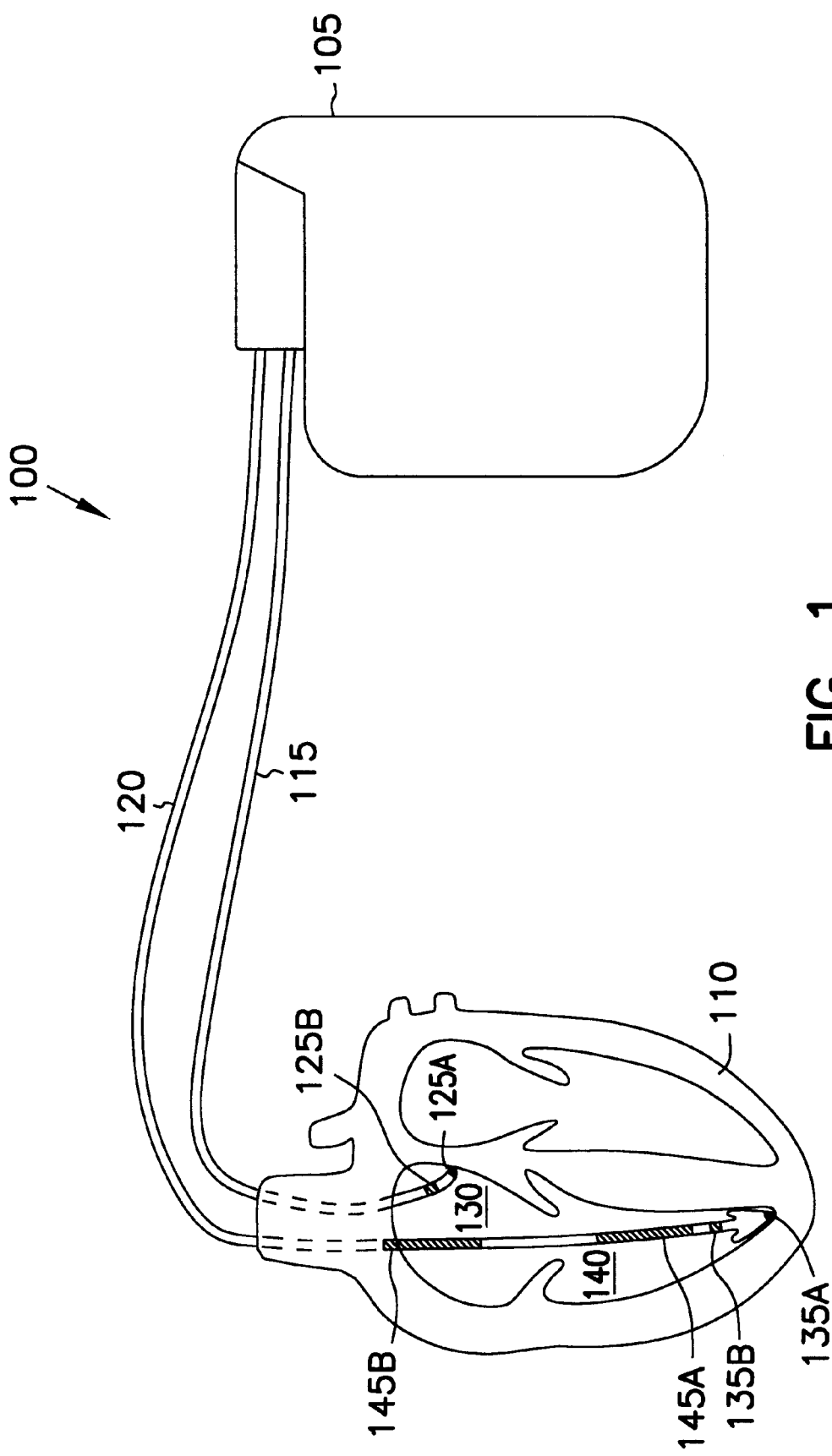
FIG. 1 is a generalized schematic diagram illustrating generally one embodiment of a portion of a cardiac rhythm management system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views.

This document describes, among other things, a cardiac rhythm management system with cross-chamber "soft blanking." The system allows sensing of desired electrical heart activity signals from an electrode located in a first chamber of the heart, while reducing unwanted noise signals originating in a second chamber of the heart. Such unwanted noise signals include, among other things, intrinsic cardiac depolarizations associated with the second chamber of the heart as well as pace pulses delivered to the second chamber of the heart.

FIG. 1 is a generalized schematic diagram illustrating generally, by way of example, but not by way of limitation, one embodiment of a portion of a cardiac rhythm management system 100. Various embodiments of system 100 include external or implantable pacers, cardioverters, defibrillators, drug delivery systems, cardiac signal monitoring or diagnostic systems, any combination of the foregoing, or any other system using or maintaining cardiac rhythms.

In the embodiment of FIG. 1, cardiac rhythm management system 100 includes a cardiac rhythm management device 105 coupled to heart 110 via a first chamber leadwire, such as atrial leadwire 115, and a second chamber leadwire, such as ventricular leadwire 120. In this example, atrial leadwire 115 includes one or more atrial electrodes 125, such as atrial tip electrode 125A and atrial ring electrode 125B, each of which is disposed in a right atrium 130 chamber of heart 110. Ventricular leadwire 120 includes one or more ventricular electrodes 135, such as ventricular tip electrode 135A and ventricular ring electrode 135B, each of which is disposed in a right ventricle 140 chamber of heart 110. Atrial leadwire 115 and ventricular leadwire 120 may also include additional electrodes, such as defibrillation electrodes 145A–B which, in this example, are located on ventricular leadwire 120 for delivering an electrical defibrillation countershock to heart 110. In the embodiment of FIG. 1, leadwires 115 and 120 each include multiple conductors that are insulated from each other for providing independent connections between each electrode and cardiac rhythm management device 105. In one embodiment, atrial tip electrode 125A and ventricular tip electrode 135A are each secured in place to heart 110, such as by a corkscrew, a barb, or similar mechanism. In another embodiment, cardiac rhythm management device 105 includes a hermetically sealed casing, a portion of which provides a conductive electrode that operates in conjunction with at least one of the electrodes disposed in heart 110 for delivering pacing and/or defibrillation pulses and/or sensing electrical heart activity signals.

Figure 2:
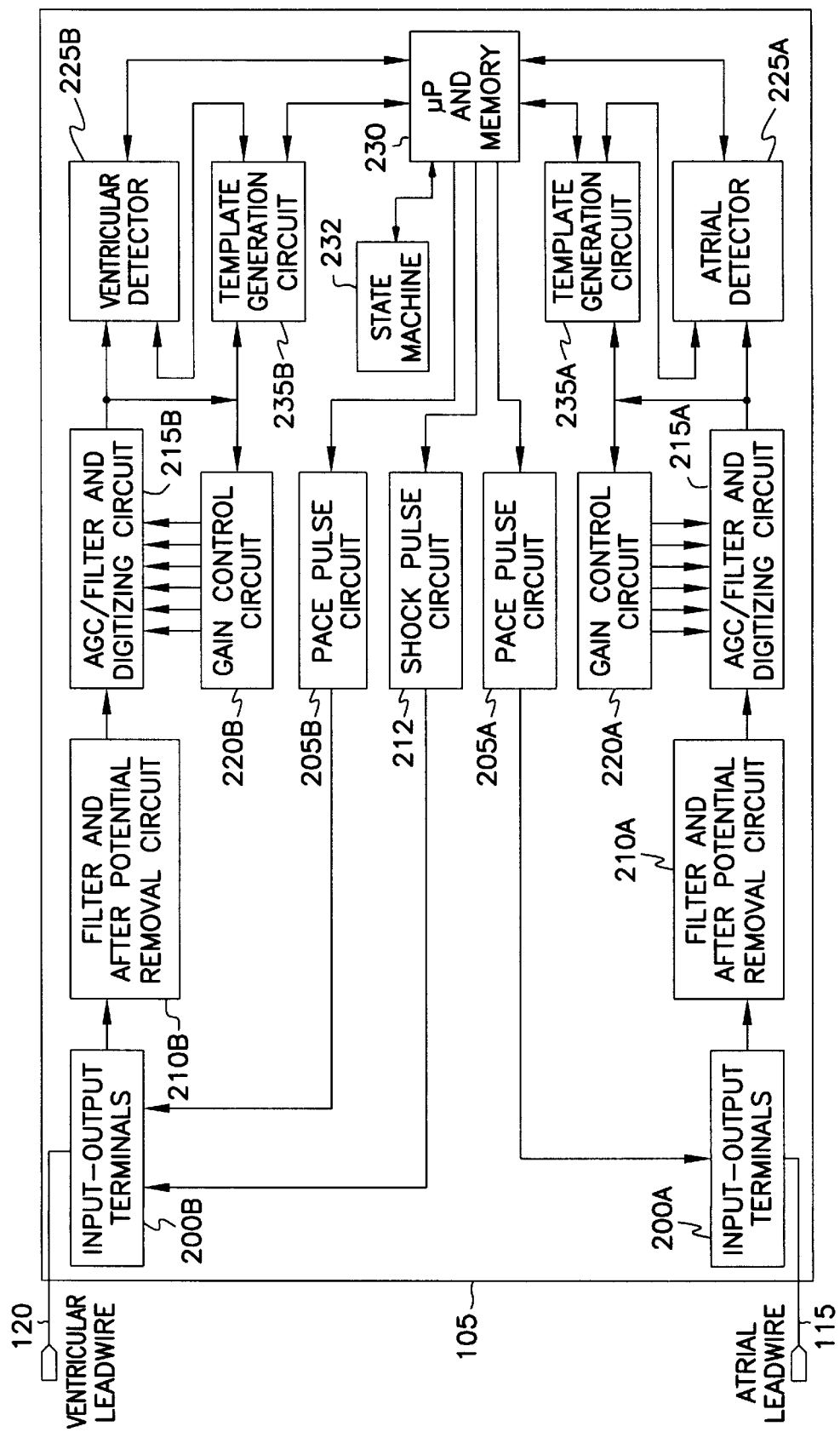
FIG. 2 is a block diagram illustrating generally one embodiment of a portion of pulse generator.

FIG. 2 is a block diagram illustrating generally, by way of example, but not by way of limitation, one embodiment of a portion of cardiac rhythm management device 105. This embodiment provides defibrillation and dual-chamber pacing, i.e., a pacer/defibrillator. However, other embodiments include a dual chamber pacer without defibrillation capability. In FIG. 2, cardiac rhythm management device 105 includes first chamber input/output terminals, such as atrial input/output terminals 200A for receiving atrial leadwire 115. Cardiac rhythm management device 105 also includes second chamber input/output terminals, such as ventricular input/output terminals 200B for receiving ventricular leadwire 120. Cardiac rhythm management device 105 is coupled to atrium 130 via atrial input/output terminals 200A and atrial leadwire 115 for delivering timed pacing pulses from pace pulse circuit 205A to atrium 130, and also for receiving, at filter circuit 210A, an electrical atrial heart activity signal from atrium 130. Similarly, cardiac rhythm management device 105 is coupled to ventricle 140 of heart 110 via ventricular input/output terminals 200B and ventricular leadwire 120, for delivering timed pacing pulses from pace pulse circuit 205B and/or defibrillation countershocks from shock pulse circuit 212 to ventricle 140 and also for receiving, at filter circuit 210B, an electrical ventricular heart activity signal from ventricle 140.

Filters 210 filter the respective electrical heart activity signals. In one embodiment, filters 210 also each include an after-potential removal circuit for removing, from such heart activity signals, after-potentials that are created by pacing pulses or defibrillation countershocks. One embodiment of such an after-potential removal circuit is described in Haefner et al. U.S. Pat. No. 5,690,683, which is assigned to the assignee of the present application, and which is incorporated herein by reference in its entirety, including its portions relating to after-potential removal systems, circuits, and methods.

Atrial automatic gain control (AGC) circuit 215A amplifies, filters, and digitizes the filtered analog atrial heart activity signal received from atrial filter 210A. Atrial gain control circuit 220A automatically adjusts the gain of atrial AGC 215A. In one embodiment, atrial gain control circuit 220A and atrial AGC 215A form a peak adjustment circuit for adjusting the gain of atrial heart activity signals (and resulting peak amplitudes of atrial depolarizations) based on one or more prior atrial depolarizations. The digitized atrial heart activity signal that is output by atrial AGC 215A is received by an atrial detector 225A. Atrial detector 225A detects atrial events indicated by (1) the digitized heart activity signal or (2) from signals received from processor 230. For example, atrial detector 225A detects atrial depolarizations, also referred to as P-waves. The atrial depolarizations are detected by comparing the digitized atrial heart activity signal received from atrial AGC 215A to a value of an atrial sensing threshold. The atrial sensing threshold is provided to atrial detector 225A from a threshold controller, such as atrial template generation circuit 235A. In one embodiment, the atrial sensing threshold is time-varying, as discussed below. In one embodiment, atrial detector 225A also detects other atrial events, such as atrial pace pulses delivered from cardiac rhythm management device 105 to atrium 130. The atrial pace pulses are detected either from (1) the digitized atrial heart activity signal output from atrial AGC 215A or (2) from a control signal received from processor 230 indicating that an atrial pace pulse was delivered by cardiac rhythm management device 105. Another possible example of an atrial event detected by atrial detector 225A is a defibrillation countershock delivered to by system 100 to heart 110.

Similarly, ventricular automatic gain control (AGC) circuit 215B amplifies, filters, and digitizes the filtered analog ventricular heart activity signal received from ventricular filter 210B. Ventricular gain control circuit 220B automatically adjusts the gain of ventricular AGC 215B. In one embodiment, ventricular gain control circuit 220B and ventricular AGC 215B form a peak adjustment circuit for adjusting a gain (and resulting peak amplitudes of ventricular depolarizations) of ventricular heart activity signals based on one or more prior ventricular depolarizations. The digitized ventricular heart activity signal that is output by AGC 215B is received by a ventricular detector 225B. Ventricular detector 225B detects ventricular events indicated by (1) the digitized heart activity signal or (2) from signals received from processor 230. For example, ventricular detector 225B detects ventricular depolarizations, also referred to as R-waves. The ventricular depolarizations are detected by comparing the digitized ventricular heart activity signal received from ventricular AGC 215B to a value of a ventricular sensing threshold provided by a threshold controller, such as template generation circuit 235B. In one embodiment, the ventricular sensing threshold is time-varying, as discussed below. In one embodiment, ventricular detector 225B also detects other ventricular events, such as ventricular pace pulses delivered from cardiac rhythm management device 105 to ventricle 140. The ventricular pace pulses are detected either from (1) the digitized ventricular heart activity signal output from ventricular AGC 215B or (2) from a control signal received from processor 230 indicating that a ventricular pace pulse was delivered by cardiac rhythm management device 105. Another possible example of a ventricular event detected by ventricular detector 225B is a defibrillation countershock delivered by system 100 to heart 110.

Processor 230 analyzes the detected atrial and ventricular events for characterizing and treating various arrhythmia conditions of heart 110. Processor 230 is capable of storing, in internal or external memory, data regarding the occurrence of atrial and ventricular events for use in arrhythmia characterization and treatment algorithms. In one embodiment, processor 230 uses a state machine 232 that places various circuits of cardiac rhythm management device 105 in desired logical states based on conditions determined by algorithms performed by processor 230.

Certain aspects of system 100 are described in Haefner et al. U.S. Pat. No. 5,620,466, entitled "Digital AGC Using Separate Gain Control and Threshold Templating," and in Haefner et al. U.S. Pat. No. 5,662,688, entitled "Slow Gain Control," and in Haefner et al. U.S. Pat. No. 5,658,317, entitled "Threshold Templating For Digital AGC," each of which is assigned to the assignee of the present patent application, and each of which is incorporated by reference herein in its entirety. It is also understood that, though FIG. 2 illustrates separate blocks for performing various functions, in other embodiments of system 100, such blocks can be combined or various ones of their operations can be carried out on processor 230.

Figure 3:
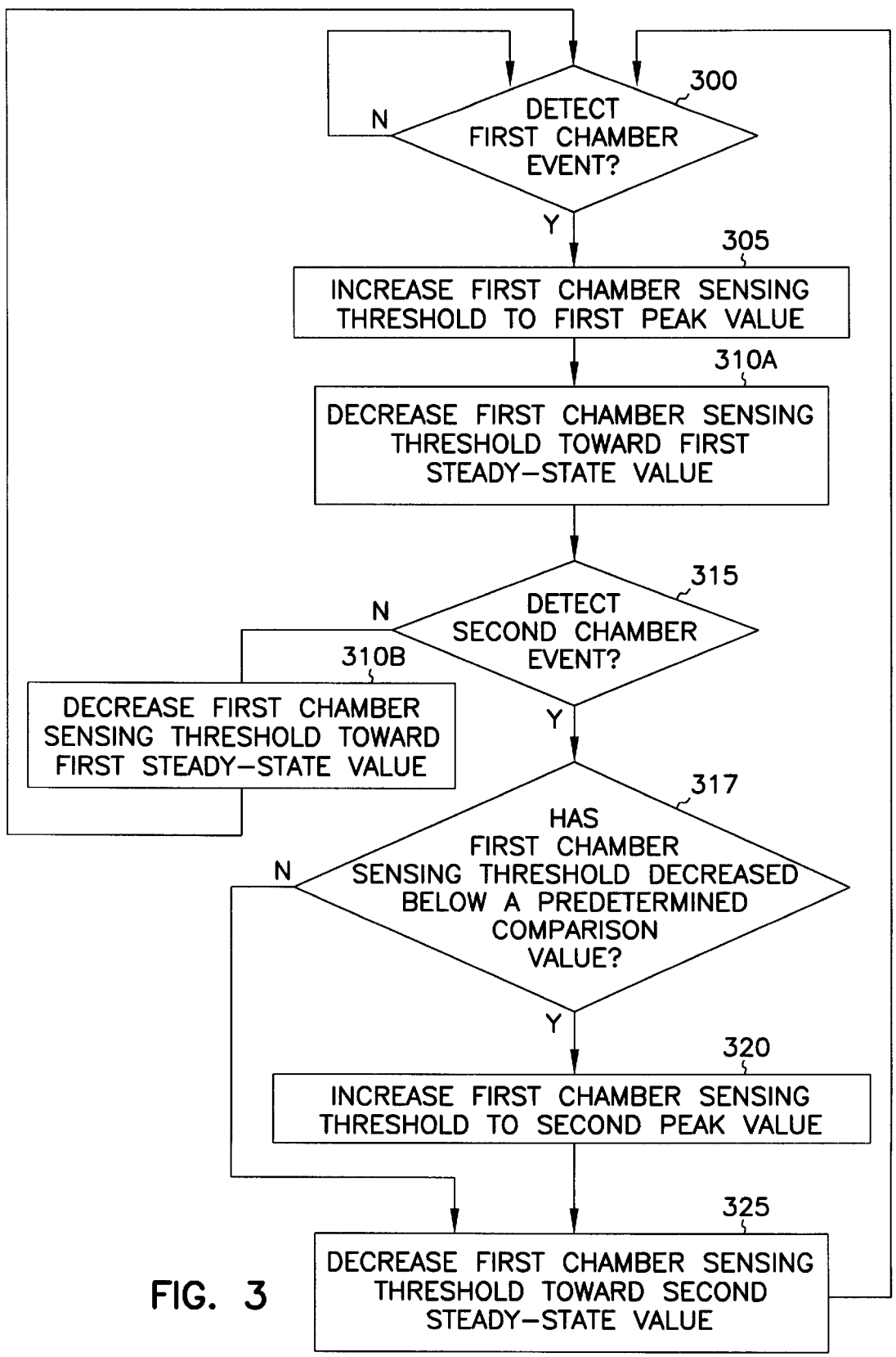
FIG. 3 is a flow chart illustrating generally one embodiment of the operation of a cardiac rhythm management system.

FIG. 3 is a flow chart illustrating generally, by way of example, but not by way of limitation, one embodiment of the operation of system 100 to provide cross-chamber "soft blanking." The soft blanking allows sensing of desired electrical heart activity signals from an electrode located in a first chamber of the heart while reducing unwanted noise signals originating in a second chamber of the heart. In FIG. 3, a first chamber event is detected at step 300. For example, in the case where the first chamber is atrium 130, the first chamber event is an atrial pace pulse or an atrial depolarization indicated by the atrial heart activity signal. Because cardiac rhythm management device 105 itself provides the atrial pace pulse, detection of the atrial pace pulse includes, in one embodiment, receiving a control signal, such as from processor 230, indicating that the atrial pace pulse was issued by cardiac rhythm management device 105.

At step 305, a first chamber sensing threshold is increased to a first peak value. For atrium 130, the atrial sensing threshold provides, in one embodiment, a time varying value to which the filtered atrial heart activity signal is compared. If the filtered atrial heart activity signal exceeds the value of the atrial sensing threshold, then atrial detector 225A declares that an atrial depolarization has been detected. By increasing the atrial sensing threshold after the detection of an atrial depolarization, atrial detector 225A is made less sensitive to subsequent variations in the atrial heart activity signal. As a result of increasing the atrial sensing threshold at step 305, larger amplitude variations in the atrial heart activity signal are required for being deemed atrial depolarizations. At step 310A, the first chamber sensing threshold is decreased toward a first steady-state value. For atrium 130, in one embodiment, this includes reducing the atrial sensing threshold in a quantized approximation of a decaying exponential function, such as described in Haefner et al. U.S. Pat. No. 5,620,466, Haefner et al. U.S. Pat. No. 5,658,317, and Haefner et al. U.S. Pat. No. 5,662,688, which were above incorporated herein by reference. As the atrial sensing threshold is decreased at step 310A–B, smaller amplitude variations in the atrial heart activity signal will be recognized as being atrial depolarizations.

At step 315, if a second chamber event is not detected, system 100 continues to decrease the first chamber sensing threshold toward the first steady-state value at step 310B, then returning to step 300 after the first chamber sensing threshold has reached the first steady-state value. If, however, a second chamber event is detected at step 315, then at step 317 system 100 determines whether the first chamber sensing threshold has decreased below a predetermined comparison value.

At step 317, if the first chamber sensing threshold has decreased below the predetermined comparison value, then the first chamber sensing threshold is again increased, at step 320, such as to a second peak value, and then decreased toward a second steady-state value at step 325. At step 317, if the first chamber sensing threshold has not decreased below the predetermined comparison value, then the first chamber sensing threshold is decreased toward the second steady-state value at step 325 without increasing the first chamber sensing threshold at step 320.

Figure 4:
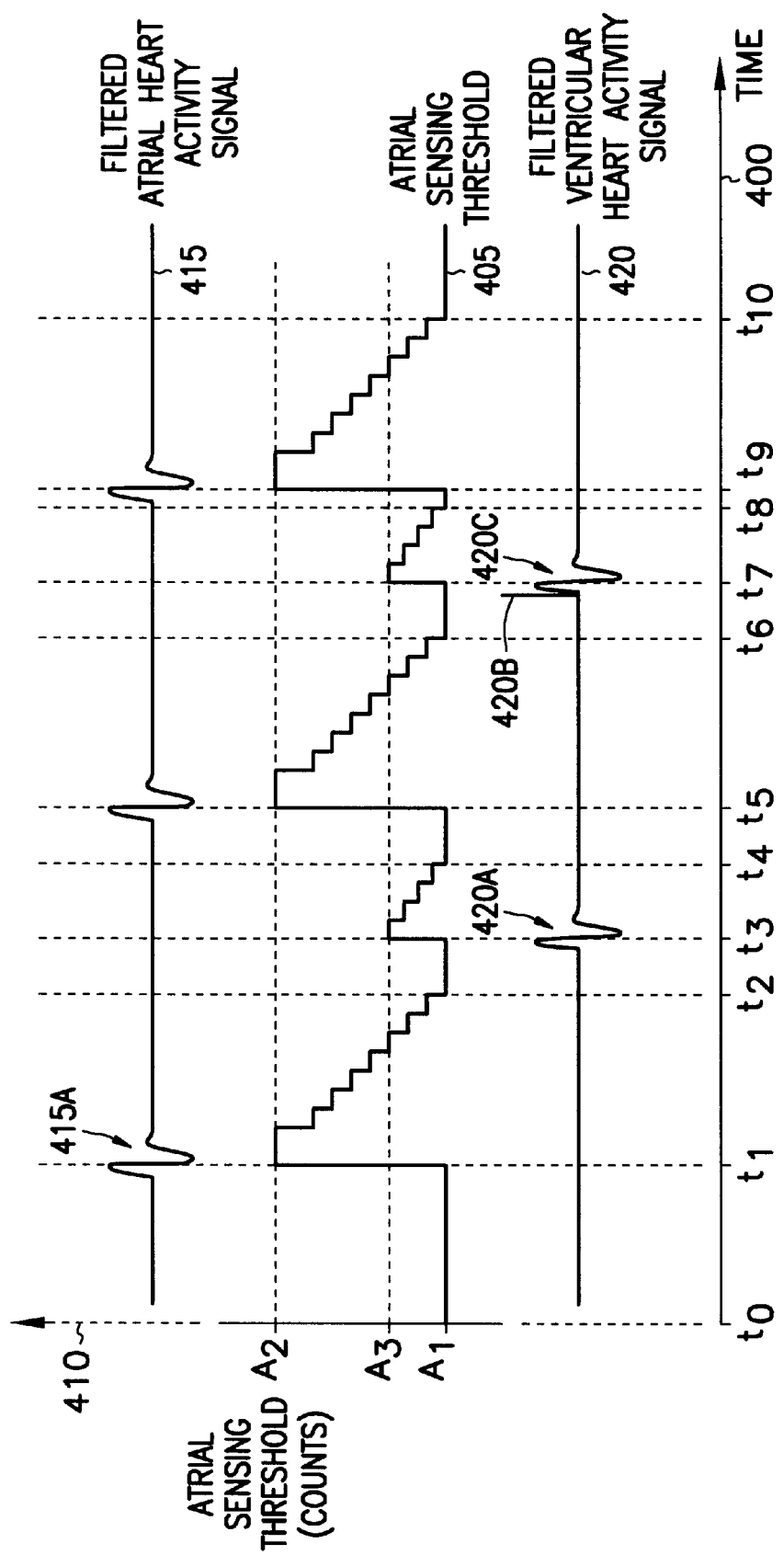
FIG. 4 is a signal flow diagram illustrating generally one embodiment of the operation of a cardiac rhythm management system in accordance with the flow chart of FIG. 3 to increase an atrial sensing threshold based on ventricular events.

FIG. 4 is a signal flow diagram illustrating generally, by way of example, but not by way of limitation, one embodiment of the operation of system 100 such as, for example, in the sequence of steps described with respect to the flow chart of FIG. 3. In FIG. 4, time is illustrated generally on horizontal axis 400, and the atrial sensing threshold 405 is a digital signal measured in digital "counts" and referenced to vertical axis 410. In one example, atrial sensing threshold 405 is an 8-bit digital "word" with values ranging between 0 counts and 127 counts. FIG. 4 also illustrates a filtered atrial heart activity signal 415 output by atrial AGC 215A, and a filtered ventricular heart activity signal 420 output by ventricular AGC 215B. In FIG. 4, atrial heart activity signal 415 and ventricular heart activity signal 420 are not referenced to vertical axis 410.

At time $t_0$, atrial sensing threshold 405 is at a first steady-state value $A_1$ which, in this example, is equal to approximately 15 counts. At time $t_1$, the atrial heart activity signal 415 includes an atrial depolarization 415A which, in this example, is an intrinsic atrial depolarization. An intrinsic depolarization is a depolarization that is produced by the heart itself, that is, without being initiated by a pace pulse delivered by system 100. Atrial detector 225A compares the amplitude of intrinsic atrial depolarization 415A to the existing value of atrial sensing threshold 405 which, at time $t_1$, is at the first steady-state value $A_1$. In this example, because the amplitude of the atrial depolarization exceeds $A_1$, atrial sensing threshold 405 is increased, at time $t_1$, to a first peak value $A_2$.

In one example, the first peak value $A_2$ of atrial sensing threshold 405 is approximately between 80 and 127 counts, and is adjusted automatically based on the amplitude of prior atrial depolarizations, such as described in Haefner et al. U.S. Pat. No. 5,658,317, which was above incorporated herein by reference. After time $t_1$, atrial sensing threshold 405 is decreased from first peak value $A_2$ toward first steady-state value $A_1$ which, in this particular example, atrial sensing threshold 405 attains at time $t_2$. In one embodiment, system 100 decreases atrial sensing threshold 405 in discrete steps as described in Haefner et al. U.S. Pat. No. 5,658,317, which was above incorporated herein by reference.

At time $t_3$, ventricular heart activity signal 420 includes an intrinsic ventricular depolarization 420A that exceeds a ventricular sensing threshold. In response to ventricular depolarization 420A, atrial sensing threshold 405 is increased to a second peak value $A_3$. In this example, second peak value $A_3$ falls between first peak value $A_2$ and first steady-state value $A_1$ of atrial sensing threshold 405.

In one example, but not by way of limitation, second peak value $A_3$ is approximately equal to ⅜ of the first peak value $A_2$ (e.g., $A_3 \approx 42$ counts and $A_2 \approx 112$ counts). As discussed above, one embodiment of system 100 provides automatic gain control (AGC), which operates to maintain the first peak value $A_2$ between an AGC lower limit (e.g., 80 counts) and an AGC upper limit (e.g., 127 counts). Maintaining $A_2$ between the upper and lower AGC limits is based on the amplitude of previously-received atrial depolarizations. As a result, during certain transient conditions (e.g., at startup), $A_2$ may fall outside the upper and lower AGC limits. In one example, when $A_2$ falls below the AGC lower limit (e.g., 80 counts), system 100 establishes the second peak value $A_3$ at approximately ⅜ of the AGC lower limit (e.g., ⅜ of 80 counts).

After time $t_3$, system 100 decreases atrial sensing threshold 405 toward a second steady-state value at time $t_4$. In this example, but not by way of limitation, the second steady-state value is approximately equivalent to the first steady state value $A_1$. In one example, atrial sensing threshold 405 is decreased toward $A_1$ in discrete steps as described in Haefner et al. U.S. Pat. No. 5,658,317, which was above incorporated herein by reference. In another embodiment, the second steady-state value is different from the first steady-state value $A_1$.

By increasing atrial sensing threshold 405, during a time period between $t_3$ and $t_4$ in response to ventricular depolarization 420A, system 100 effectively provides a cross-chamber soft-blanking function. The increased atrial sensing threshold 405 reduces the sensitivity of atrial detector 225A when ventricular detector 225B indicates a ventricular depolarization. The ventricular depolarization results in far-field noise that may be improperly sensed by atrial detector 225A if atrial sensing threshold 405 were not increased as described above. However, as illustrated in FIG. 4, atrial heart activity signal 415 is not completely ignored during the time period between $t_3$ and $t_4$. Instead, atrial detector 225A remains capable of detecting an atrial depolarization during the time period between $t_3$ and $t_4$, provided that the atrial depolarization exceeds the value of atrial sensing threshold 405 during that time.

Figure 5:
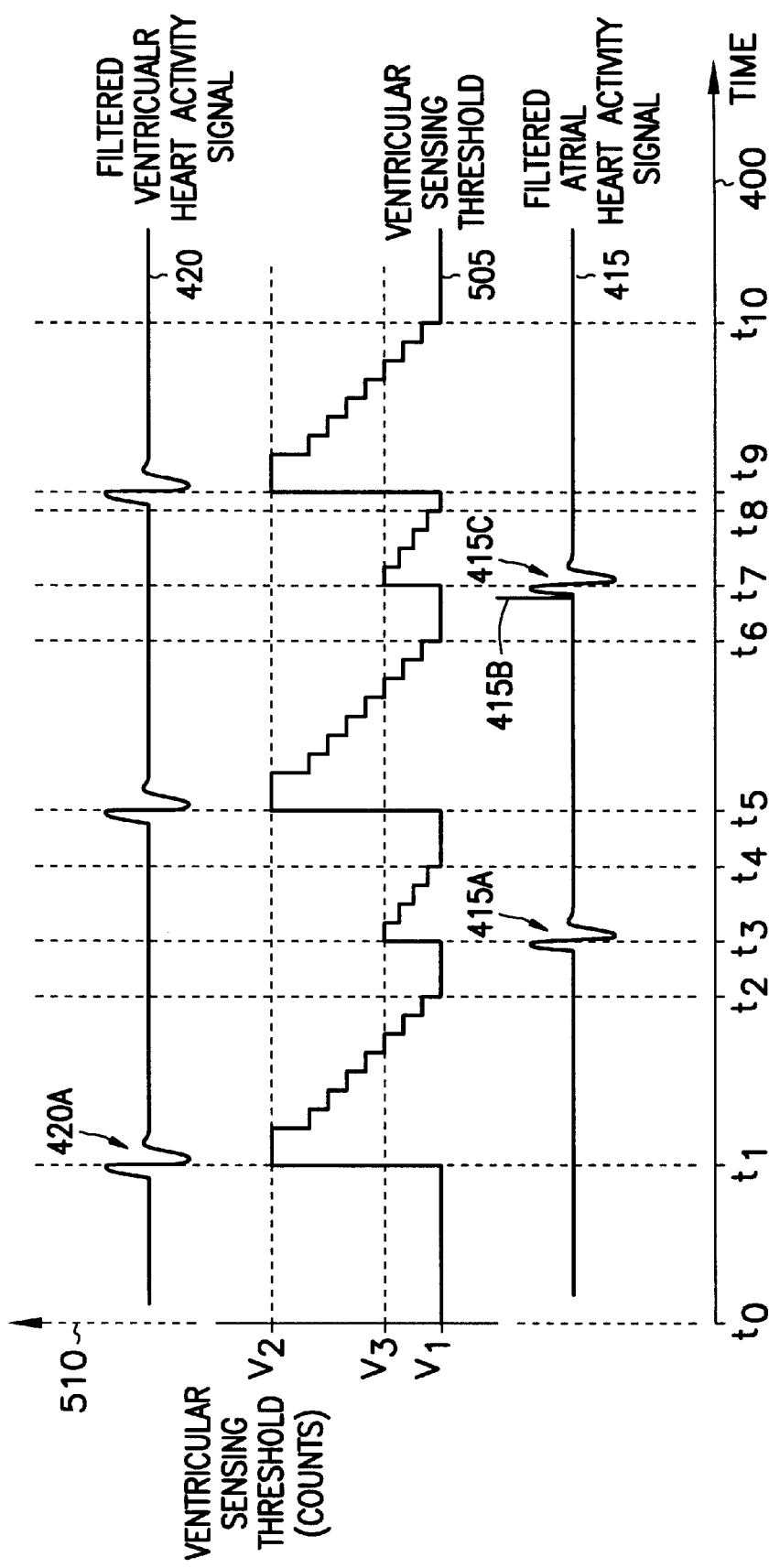
FIG. 5 is a signal flow diagram illustrating generally one embodiment of the operation of a cardiac rhythm management system in accordance with the flow chart of FIG. 3 to increase the ventricular sensing threshold based on atrial events.

Increasing the value of the atrial sensing threshold 405, in response to a ventricular event, to a value that still allows effective sensing of the atrial heart activity signal 415 is one example of what is referred to as cross-chamber soft blanking herein. It is understood that cross-chamber soft blanking would also include, for example, increasing the value of a ventricular sensing threshold, in response to an atrial event, to a value that still allows effective sensing of the ventricular heart activity signal 420. FIG. 5 is a signal flow diagram that follows analogously from the description of FIG. 4, in which a ventricular sensing threshold 505 is increased and then decreased, during a time period between $t_3$ and $t_4$, in response to atrial depolarization 415A. FIG. 5 illustrates one example of carrying out the technique of FIG. 3 where the first chamber is ventricle 140 and the second chamber is atrium 130. By comparison, FIG. 4 illustrated one example of carrying out the technique of FIG. 3 where the first chamber was atrium 130 and the second chamber is ventricle 140.

FIG. 4 also illustrates cross-chamber soft blanking during a time period between $t_7$ and $t_8$ in response to a ventricular event that includes a ventricular pace pulse 420B that triggers a resulting ventricular depolarization 420C. In this case, because system 100 issues the ventricular pace pulse 420B, it is not necessary to detect the evoked ventricular depolarization 420C before increasing the atrial sensing threshold 405 to $A_3$. Instead, processor 230 issues a control signal to template generation circuit 235A when ventricular pace pulse 420B is issued. Based on this control signal representing the delivery of ventricular pace pulse 420B, the atrial sensing threshold 405 is increased to $A_3$. Similarly, FIG. 5 also illustrates cross-chamber soft blanking during a time period between $t_7$ and $t_8$ in response to an atrial event that includes an atrial pace pulse 415B that triggers a resulting atrial depolarization 415C. In this case, atrial pace pulse 415B is a second chamber event that results in the increase in the ventricular sensing threshold 505.

Figure 6:
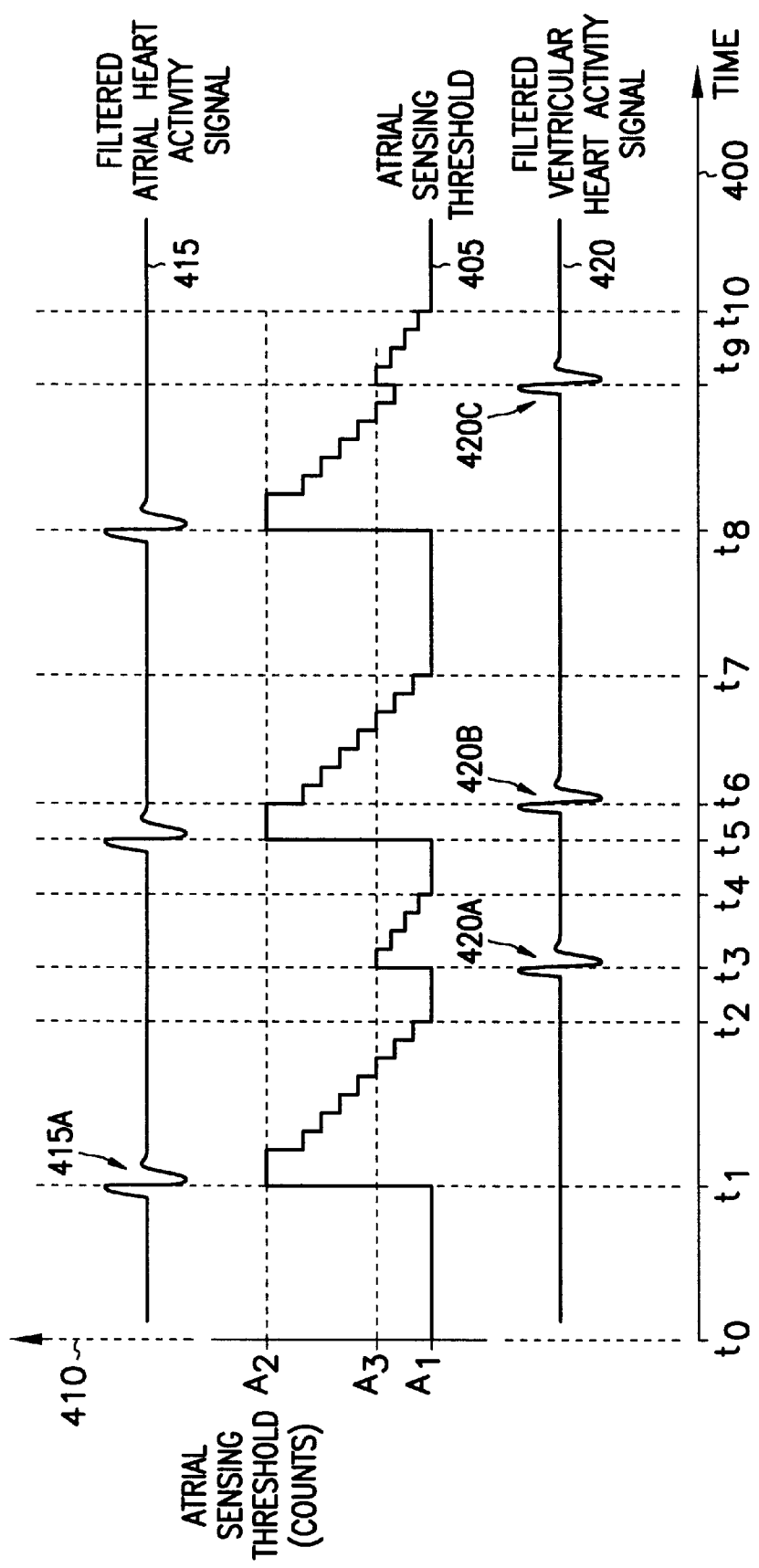
FIG. 6 is a signal flow diagram illustrating generally one embodiment of the operation a cardiac rhythm management system in accordance with the flow chart of FIG. 3.

FIG. 6 is a signal flow diagram, similar to FIG. 4, illustrating by way of example, but not by way of limitation one embodiment of the operation of system 100 as described with respect to FIG. 3. The signals of FIG. 6 display similar characteristics to those of FIG. 4 until $t_6$, at which time intrinsic ventricular depolarization 420B occurs. Ventricular depolarization 420B is a second chamber event that is detected at step 315 of FIG. 3. Because, at step 317 of FIG. 3, the first chamber sensing threshold (e.g., atrial sensing threshold 405 in FIG. 6) has not decreased below a predetermined comparison value (which in this particular example is equal to second peak value $A_3$) step 320 of FIG. 3 is bypassed. In other words, at time $t_6$, the atrial sensing threshold 405 is not increased because it still exceeds a predetermined comparison value that, in this example, is equal to second peak value $A_3$. Instead, system 100 continues to decrease the atrial sensing threshold 405 toward a second steady-state value which, in this example, is equivalent to first steady-state value $A_1$ attained at time $t_7$.

Similarly, at time $t_9$, intrinsic ventricular depolarization 420C is a second chamber event that is detected at step 315 of FIG. 3. At step 317 of FIG. 3, the first chamber sensing threshold (e.g., atrial sensing threshold 405 in FIG. 6) has decreased below a predetermined comparison value that, in this example, is set equal to the second peak value $A_3$. Consequently, at time $t_9$, the first chamber sensing threshold (e.g., atrial sensing threshold 405 in FIG. 6) is increased, such as described with respect to step 320 of FIG. 3. Atrial sensing threshold 405 is increased to a second peak value $A_3$ that, in this example, is approximately equal to the predetermined comparison value at step 317 of FIG. 3. However, it is understood that the predetermined comparison value for triggering an increased atrial sensing threshold 405 need not necessarily be the same value of the atrial sensing threshold 405 as the second peak value $A_3$ to which the atrial sensing threshold 405 is increased.

FIGS. 3–6 separately illustrate, among other things, the use of cross-chamber soft blanking in atrium 130, in response to ventricular pacing and intrinsic depolarization events, or in ventricle 140, in response to atrial pacing and intrinsic depolarization events. However, it is understood that in one embodiment, system 100 carries out cross-chamber soft blanking simultaneously in multiple chambers of heart 110.

Figure 7:
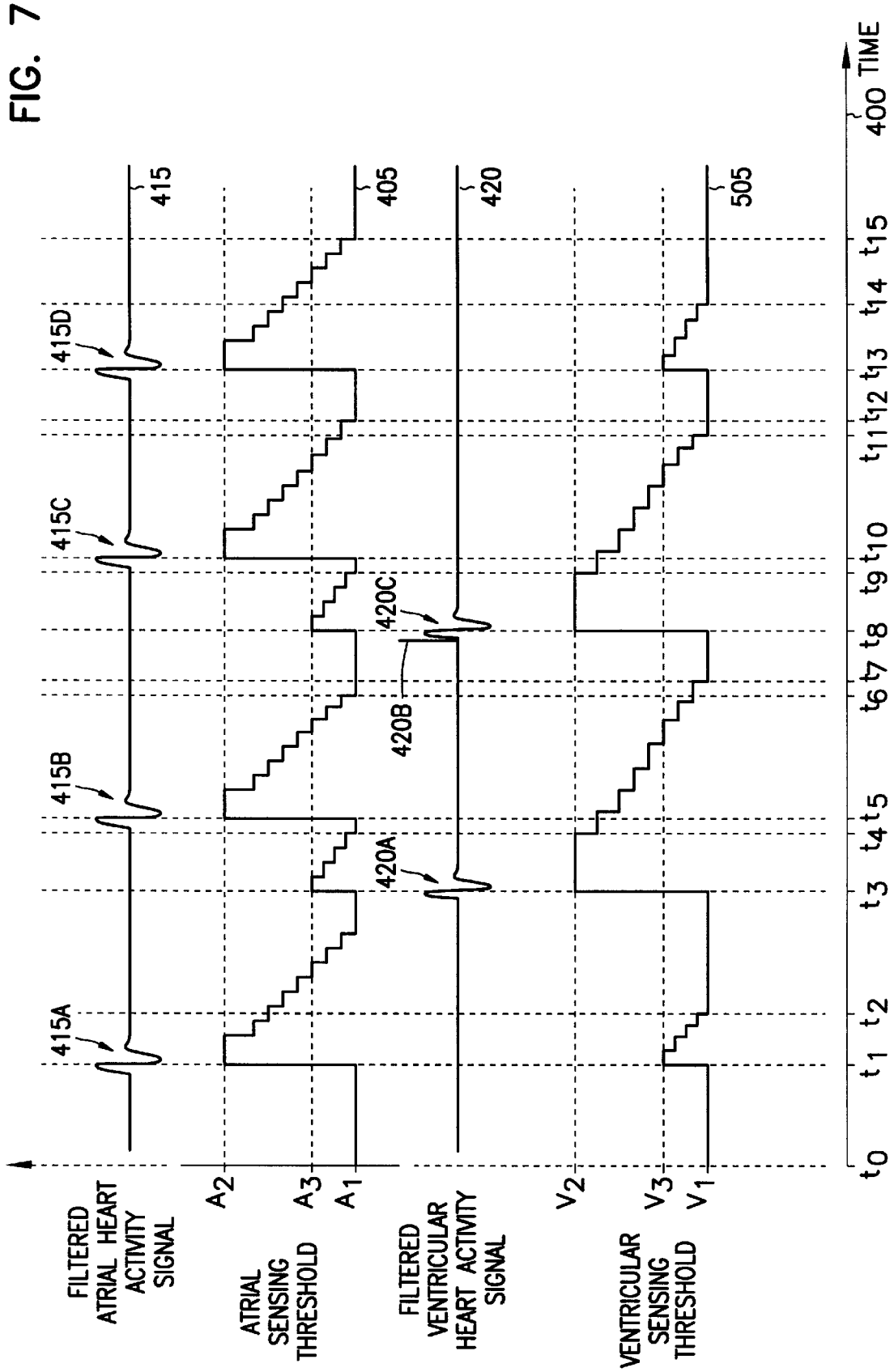
FIG. 7 is a signal flow diagram illustrating generally one embodiment of the operation of a cardiac rhythm management system to increase an atrial sensing threshold based on ventricular events, and to increase a ventricular sensing threshold based on atrial events.

FIG. 7 is a signal flow diagram illustrating generally, by way of example, but not by way of limitation, one embodiment of operating system 100 for cross-chamber soft blanking simultaneously in both atrium 130 and ventricle 140. In FIG. 7, at time $t_1$, atrial heart activity signal 415 includes an intrinsic atrial depolarization 415A, which triggers in increase in atrial sensing threshold 405 from $A_1$ to $A_2$, from which atrial sensing threshold 405 subsequently begins to decrease back toward $A_1$. Atrial depolarization 415A also triggers cross-chamber soft-blanking. Because, at time $t_1$, ventricular sensing threshold 505 is below a predetermined comparison value (e.g., below $V_3$), system 100 increases ventricular sensing threshold 505 from $V_1$ to $V_3$, from which ventricular sensing threshold 505 subsequently begins to decrease back toward $V_1$.

At time $t_3$, ventricular heart activity signal 420 indicates an intrinsic ventricular depolarization 420A, which triggers an increase in ventricular sensing threshold 505 from $V_1$ to $V_2$, from which ventricular sensing threshold 505 begins to decrease back toward $V_1$. Ventricular depolarization 420A also triggers cross-chamber soft-blanking. Because, at time $t_3$, atrial sensing threshold 405 is below a predetermined comparison value (e.g., below $A_3$), system 100 increases atrial sensing threshold 405 from $A_1$ to $A_3$, from which atrial sensing threshold 405 begins to decrease back toward $A_1$.

At time $t_5$, atrial heart activity signal 415 indicates an intrinsic atrial depolarization 415B, which triggers an increase in atrial sensing threshold 405 from $A_1$ to $A_2$, from which atrial sensing threshold 405 begins to decrease back toward $A_1$. However, atrial depolarization 415B does not trigger a cross-chamber increase in ventricular sensing threshold 505 because, at time $t_5$, ventricular sensing threshold 505 already exceeds a predetermined value (e.g., $V_3$).

At time $t_8$, ventricular heart activity signal 420 indicates that a ventricular pace pulse 420B was delivered, evoking a resulting ventricular depolarization 420C. Ventricular pace pulse 420B triggers an increase in ventricular sensing threshold 505 from $V_1$ to $V_2$, from which ventricular sensing threshold 505 begins to decrease back toward $V_1$. Ventricular pace pulse 420B also triggers a cross-chamber soft-blanking. Because, at time $t_8$, atrial sensing threshold 405 is below a predetermined comparison value (e.g., below $A_3$), system 100 increases atrial sensing threshold 405 from $A_1$ to $A_3$, from which atrial sensing threshold 405 begins to decrease back toward $A_1$.

At time $t_{10}$, atrial heart activity signal 415 indicates an intrinsic atrial depolarization 415C, which triggers an increase in atrial sensing threshold 405 from $A_1$ to $A_2$, from which atrial sensing threshold 405 begins to decrease back toward $A_1$. However, atrial depolarization 415C does not trigger a cross-chamber increase in ventricular sensing threshold 505 because, at time $t_{10}$, ventricular sensing threshold 505 already exceeds a predetermined value (e.g., $V_3$).

At time $t_{13}$, atrial heart activity signal 415 includes an intrinsic atrial depolarization 415D, which triggers in increase in atrial sensing threshold 405 from $A_1$ to $A_2$, from which atrial sensing threshold 405 subsequently begins to decrease back toward $A_1$. Atrial depolarization 415D also triggers a cross-chamber soft-blanking. Because, at time $t_{13}$, ventricular sensing threshold 505 is below a predetermined comparison value (e.g., below $V_3$), system 100 increases ventricular sensing threshold 505 from $V_1$ to $V_3$, from which ventricular sensing threshold 505 subsequently begins to decrease back toward $V_1$.

FIG. 7 illustrated, among other things, cross-chamber soft blanking being carried out simultaneously in two chambers of heart 110. It is understood, however, that such cross-chamber soft blanking can also be carried out simultaneously in more than two chambers of heart 110. Similarly, such soft blanking can be carried out in a single chamber of heart 110, as illustrated in FIGS. 3–6, but based on cross-chamber signals received from more than one other chamber of heart 110. Moreover, even though the term heart chamber is used, it is understood that signals associated with a particular heart chamber may be obtained via an electrode that is not actually disposed in the heart chamber, but is instead disposed near enough to the heart chamber (e.g., an epicardial electrode) to acquire signals associated with that heart chamber.

Figure 8:
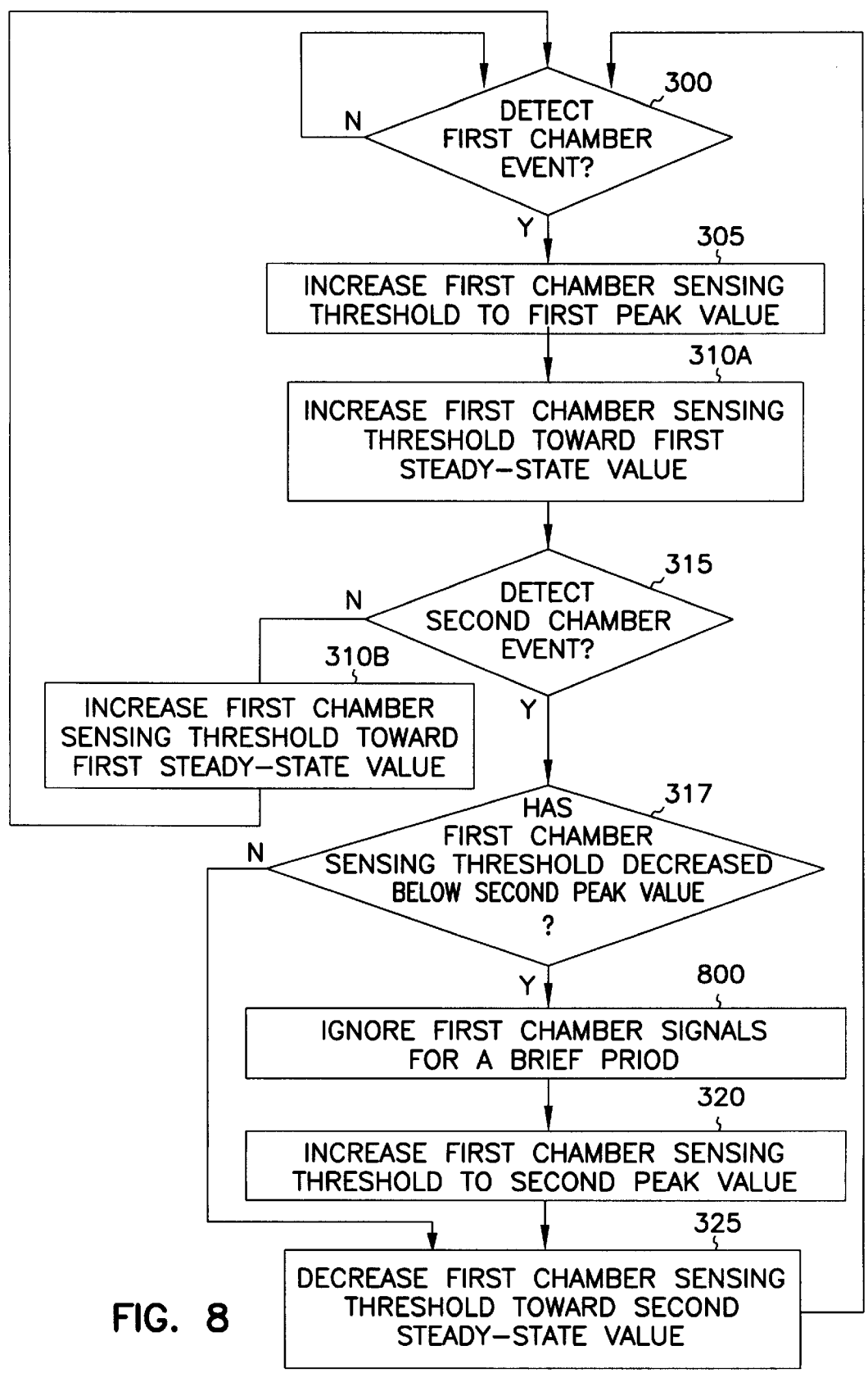
FIG. 8 is a flow chart illustrating another embodiment of operation of a cardiac rhythm management system.

FIG. 8 is a flow chart illustrating generally, by way of example, but not by way of limitation, another embodiment of operation of system 100. Steps 300, 305, 310A–B, 315, and 317 are as described with respect to FIG. 3. If system 100 detects a second chamber event, at step 315, and the first chamber sensing threshold has decreased below the second peak value, at step 317, then first chamber signals are ignored ("blanked" or "hard-blanked") for a short period of time (e.g., less than approximately between 5–15 milliseconds) at step 800. Next, the first chamber sensing threshold is increased (i.e., with respect to the steady-state value) to the third peak value at step 320. If, at step 317, the first chamber sensing threshold has not decreased below the second peak value, then system 100 continues to decrease the first chamber sensing threshold toward the second steady-state value, at step 325, without briefly ignoring the first chamber signals at step 800 and without first increasing the first chamber sensing threshold at step 320.

Figure 9:
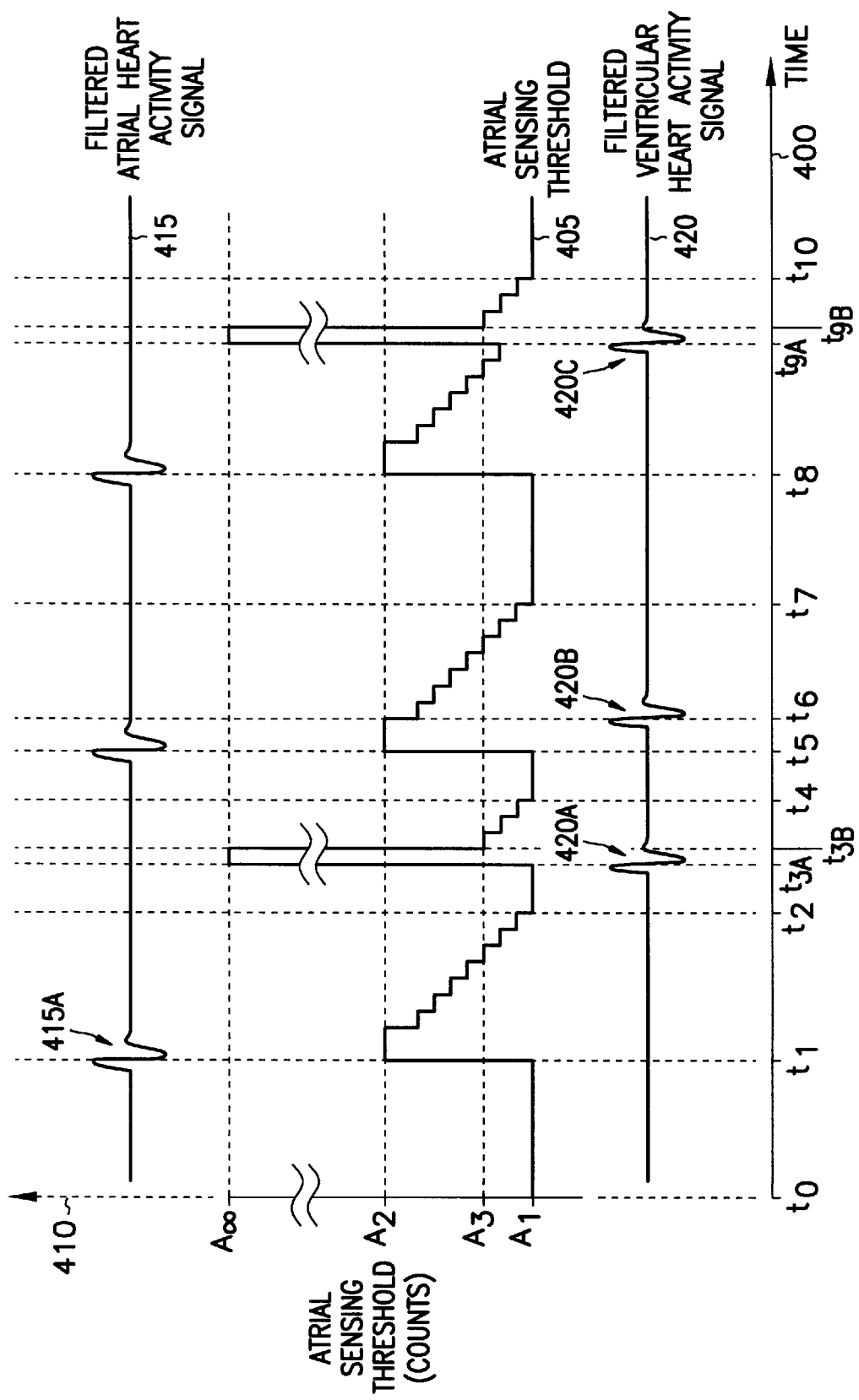
FIG. 9 is a signal flow diagram, illustrating generally one embodiment of operation of a cardiac rhythm management system as described with respect to the flow chart of FIG. 8.

FIG. 9 is a signal flow diagram, illustrating generally, by way of example, but not by way of limitation one embodiment of operation of system 100 as described with respect to FIG. 8. The signals of FIG. 9 display similar characteristics to those of FIG. 6 until $t_{3A}$, at which time intrinsic ventricular depolarization 420A occurs. This triggers a cross-chamber blanking that includes ignoring signals received from atrium 130 for a brief period of time between $t_{3A}$ and $t_{3B}$, such time being shorter than approximately between 5–15 milliseconds. In FIG. 9, this is represented by an infinite value, $A_\infty$, of atrial sensing threshold 405. An alternative technique for effectively ignoring signals received from atrium 130 between $t_{3A}$ and $t_{3B}$ is to increase atrial sensing threshold 405 to its maximum value (in this particular 8-bit example, the maximum value of atrial sensing threshold 405 corresponds to 127 counts) during this hard-blanking time period, rather than to the infinite value $A_\infty$. In FIG. 9, atrial sensing threshold 405 then is increased (with respect to steady-state baseline value $A_1$) to $A_3$, at time $t_{3B}$, and then decreased toward $A_1$. A similar cross-chamber soft-blanking (preceded by a very brief hard-blanking period during which first chamber signals are ignored) occurs between times $t_{9B}$ and $t_{10}$. Also in FIG. 9, at time $t_6$, intrinsic ventricular depolarization 420B occurs. However, at that time atrial sensing threshold 405 has not decreased below a predetermined value (e.g., $A_3$), so no cross-chamber blanking is performed.

The above-described embodiment includes hard-blanking for a short time period (e.g., approximately between 5–15 milliseconds) followed by a soft-blanking period. This embodiment is effective because it is closely tailored to the cross-chamber noise likely to be present. The cross-chamber noise artifact is typically most problematic during a time period of approximately 6 milliseconds after the cross-chamber event, with smaller noise artifacts being present during a time period of as long as 100 milliseconds after the cross-chamber event. As illustrated in FIG. 9, the hard-blanking effectively completely ignores all signals during the relatively short (e.g., approximately between 5–15 millisecond) hard-blanking period when the cross-chamber noise artifact is likely to be most problematic. The subsequent soft-blanking period still offers some measure of cross-chamber noise immunity without completely blinding system 100 to actual atrial signals.

Figure 10:
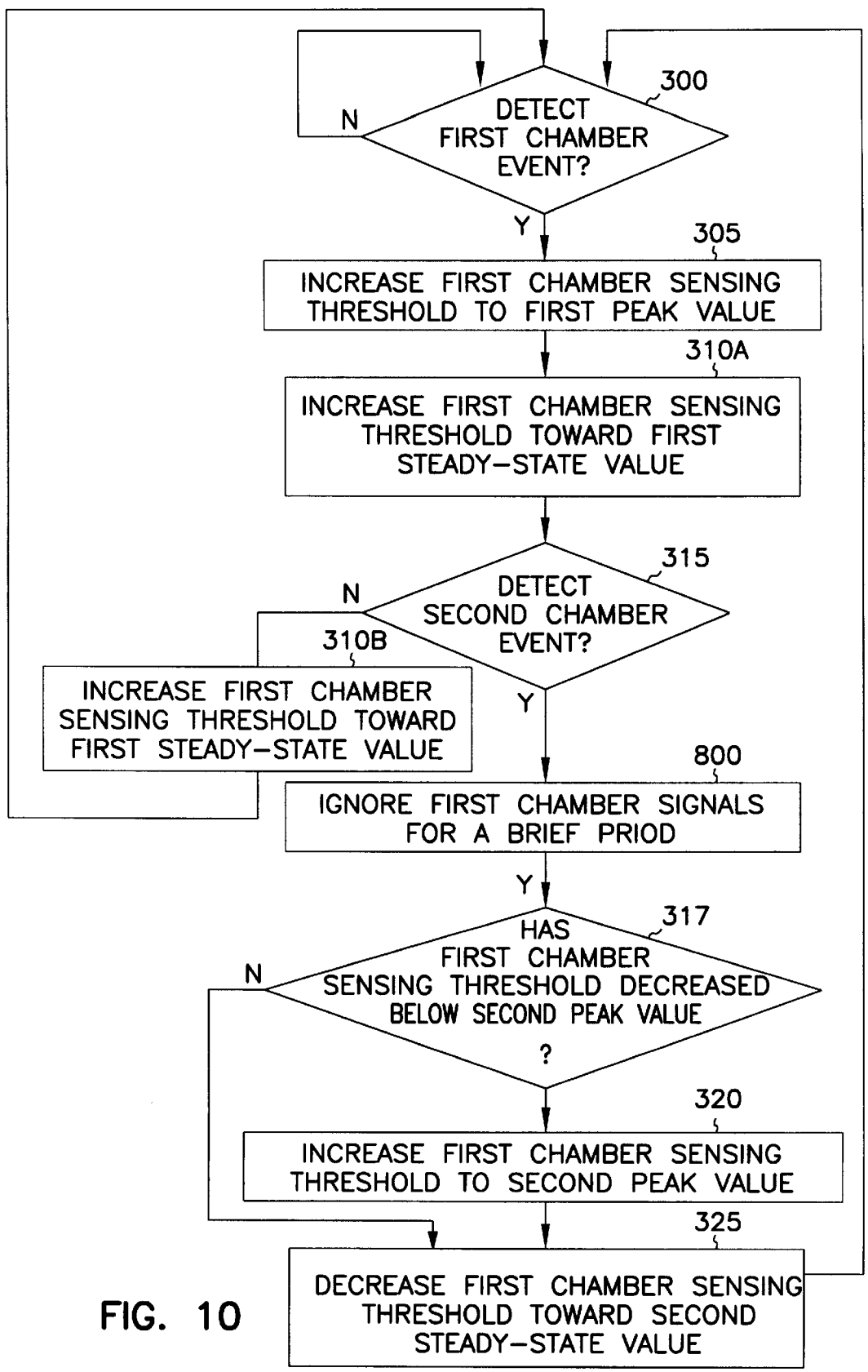
FIG. 10 is a flow chart illustrating generally another embodiment of operation of a cardiac rhythm management system.
Figure 11:
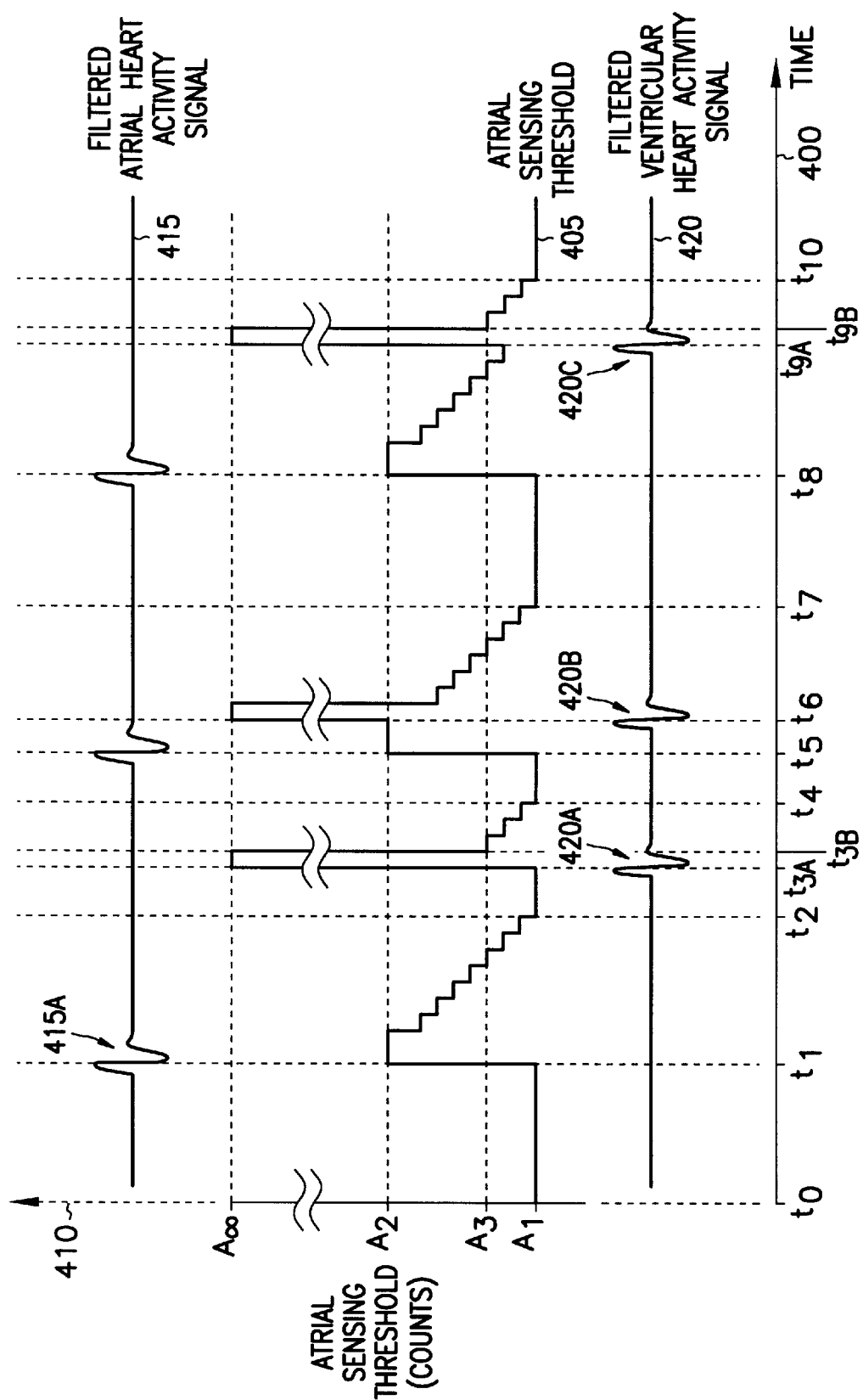
FIG. 11 is a signal flow diagram illustrating generally one embodiment of operation of a cardiac rhythm management system as described with respect to the flow chart of FIG. 10.

FIG. 10 is a flow chart illustrating generally, by way of example, but not by way of limitation, another embodiment of operation of system 100. FIG. 10 is similar to FIG. 8, except that in FIG. 10, step 800 of ignoring first chamber signals for a brief period is performed upon any detection of a second chamber event at step 315. FIG. 11 is a signal flow diagram, illustrating generally, by way of example, but not by way of limitation one embodiment of operation of system 100 as described with respect to FIG. 10. The signals of FIG. 11 display similar characteristics to those of FIG. 9, except that in FIG. 11, a short cross-chamber "hard blank" results from intrinsic ventricular depolarization 420B at time $t_6$ even though atrial sensing threshold 405 has not decreased below the predetermined comparison value (e.g., $A_3$) at time $t_6$.

Figure 12:
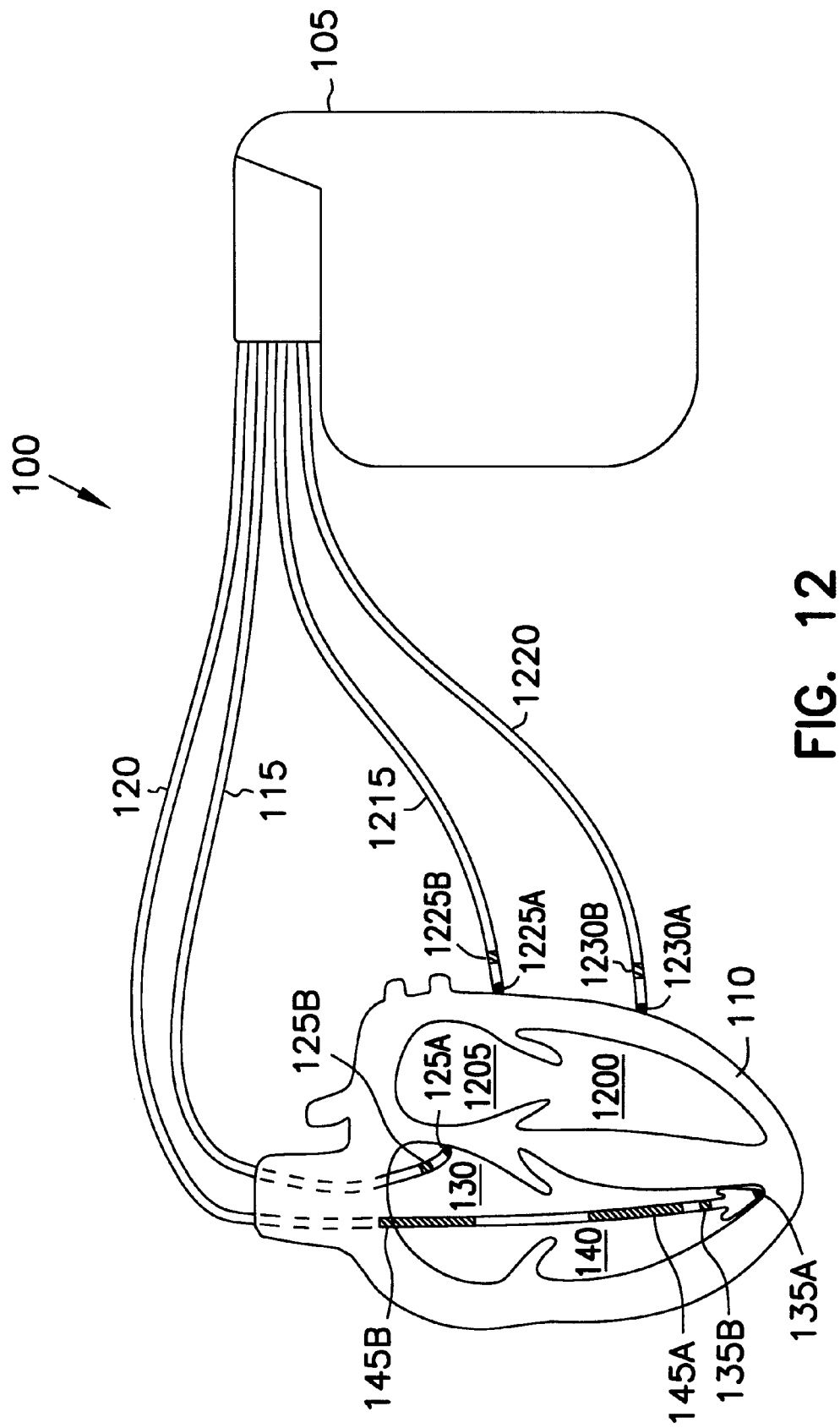
FIG. 12 is a generalized schematic diagram illustrating a cardiac rhythm management system including leadwires associated with a left atrium and/or left ventricle.

FIG. 12 is a generalized schematic diagram illustrating generally, by way of example, but not by way of limitation, another embodiment of a portion of cardiac rhythm management system 100 including epicardial or other leadwires for obtaining signals from or delivering therapy to left ventricle 1200 and left atrium 1205. FIG. 12 illustrates, by way of example, but not by way of limitation, epicardial left atrial leadwire 1215 including pacing electrodes 1225A–B, and epicardial left ventricular leadwire 1220 including pacing electrodes 1230A–B. In an alternative embodiment, left ventricular leadwire 1220 is transvenously introduced through right atrium 130 and into a portion of a coronary sinus that is located near left ventricle 1200.

CONCLUSION

The above-described cardiac rhythm management system provides, among other things, cross-chamber "soft blanking." The system allows sensing of desired electrical heart activity signals from an electrode located in or near a first chamber of the heart, while reducing unwanted noise signals originating in or near a second chamber of the heart. Such unwanted noise signals include, among other things, intrinsic cardiac depolarizations associated with the second chamber of the heart as well as pace pulses delivered to the second chamber of the heart. The soft-blanking advantageously minimizes the erroneous sensing of second-chamber depolarizations as first-chamber depolarizations, which could result in a pace pulse being inappropriately withheld from the first chamber when it should have been delivered. Moreover, because the detection of a cross-chamber event in the second chamber does not result in completely ignoring signals in the first chamber for an appreciable amount of time, actual first chamber events are less likely to escape detection.

Examples of the system were described above, by way of example, but not by way of limitation, for blanking in or near the first heart chamber (e.g., the right atrium and the right ventricle, respectively) in response to cross-chamber signals associated with the second heart chamber (e.g., the right ventricle and right atrium, respectively). However, the system is more generally applicable to providing soft-blanking in or near any one of a right atrium, a right ventricle, a left atrium, or a left ventricle first heart chambers, in response to a second chamber event associated with a different one of the above-listed heart chambers.

For example, in other embodiments, the cardiac rhythm management system is used to provide soft-blanking in the right atrium or right ventricle of signals originating elsewhere (e.g., in the left ventricle, left atrium, coronary sinus, or elsewhere). In one example of such operation, the system is used for treating congestive heart failure (CHF). In one embodiment, the sensing of signals associated with the left ventricle is obtained via a pacing lead inserted into the coronary sinus. In another embodiment, the sensing of signals associated with the left ventricle is obtained via an electrode located on a portion of the outer wall of the heart that is near the left ventricle. The soft blanking is used in one or more of the right atrium, right ventricle, or left ventricle, to increase noise-immunity to far-field signals received from the others of these chambers. The cardiac rhythm management system can also be used to provide soft-blanking elsewhere, that is, other than in the right atrium and right ventricle. Particular embodiments of the cardiac rhythm management are summarized below.

One aspect of the system provides, among other things, a method of detecting electrical first and second chamber heart activity signals associated with first and second chambers of a heart, respectively. The system detects a first chamber event indicated by the first chamber heart activity signal. In response to the first chamber event, the system increases a time-varying first chamber sensing threshold to a first peak value. Next, the system decreases the first chamber sensing threshold with time from the first peak value toward a first steady-state value. The system detects a second chamber event indicated by the second chamber heart activity signal. In response to the second chamber event, the system increases the first chamber sensing threshold to a second peak value, which is between the first peak and first steady-state values. Next, the system decreases the first chamber sensing threshold with time from the second peak value toward a second steady-state value.

Various further embodiments include detecting the first chamber event by detecting one of a first chamber pace pulse or a first chamber depolarization that exceeds the first chamber sensing threshold. Detecting the second chamber event includes detecting one of a second chamber pace pulse or a second chamber depolarization that exceeds a time varying second chamber sensing threshold. Detecting the first and second chamber events includes detecting the first chamber event in or near one of a right atrium, a right ventricle, a left atrium, or a left ventricle heart chambers, and detecting the second chamber event in or near a different one of the above-listed heart chambers. In one embodiment, the method further includes, in response to detecting the second chamber event, ignoring the first chamber heart activity signal for a time period of less than approximately 15 milliseconds before performing the soft-blanking.

In various further embodiments, the first steady-state value of the first chamber sensing threshold is approximately equal to the second steady-state value of the first chamber sensing threshold. The second peak value of the first chamber sensing threshold is approximately ⅜ of the first peak value of the first chamber sensing threshold.

Another aspect of the system provides, among other things, a method of detecting electrical first chamber and second chamber heart activity signals associated with first and second heart chambers, respectively. The system detects a first chamber event indicated by the first chamber heart activity signal. The first chamber event consists essentially of one of a first chamber pace pulse or a first chamber depolarization that exceeds a time-varying first chamber sensing threshold. In response to the first chamber event, the system increases the first chamber sensing threshold to a first peak value. Then, the system decreases the first chamber sensing threshold with time from the first peak value toward a first steady-state value. The system detects a second chamber event indicated by the second chamber heart activity signal. The second chamber event consists essentially of one of a second chamber pace pulse or a second chamber depolarization that exceeds a time-varying second chamber sensing threshold. The system increases, in response to the second chamber event, the first chamber sensing threshold to a second peak value, which is between the first peak and first steady-state values. Then, the system decreases the first chamber sensing threshold with time from the second peak value toward a second steady-state value. In response to the second chamber event, the system then increases the second chamber sensing threshold to a third peak value. Then, the system decreases the second chamber sensing threshold from the third peak value toward a third steady-state value.

Various further embodiments include decreasing the first chamber sensing threshold in discrete steps from the first peak value toward the first steady-state value. The second chamber sensing threshold is decreased in discrete steps from the third peak value toward the third steady-state value. In one embodiment, the first and second steady-state values of the first chamber sensing threshold are approximately equal. In another embodiment, the first steady-state value of the first chamber sensing threshold is different from the third steady-state value of the second chamber sensing threshold. In a further embodiment, the second peak value of the first chamber sensing threshold is approximately ⅜ of the first peak value of the first chamber sensing threshold.

Another aspect of the system provides, among other things, a method of detecting electrical first chamber and second chamber heart activity signals associated with first and second heart chambers, respectively. The system detects a first chamber event indicated by the first chamber heart activity signal. The first chamber event consists of one of a first chamber pace pulse or a first chamber depolarization that exceeds a time-varying first chamber sensing threshold. In response to the first chamber event, the system increases the first chamber sensing threshold to a first peak value. Then, the system decreases the first chamber sensing threshold with time from the first peak value toward a first steady-state value. The system detects a second chamber event indicated by the second chamber heart activity signal. The second chamber event consists of one of a second chamber pace pulse or a second chamber depolarization that exceeds a time-varying second chamber sensing threshold. If the first chamber sensing threshold has decreased approximately below a predetermined comparison value, which is between the first peak and first steady-state values, then the system increases, in response to the second chamber event, the first chamber sensing threshold to a second peak value. The second peak value is between the first peak and first steady-state values. Then, the system decreases the first chamber sensing threshold with time from the second peak value toward a second steady-state value.

In various further embodiments, the predetermined comparison value is approximately equivalent to the second peak value of the first chamber sensing threshold. The first and second steady-state values of the first chamber sensing threshold are approximately equivalent. The system decreases the first chamber sensing threshold in discrete steps from the first peak value toward the first steady-state value. In response to the second chamber event, the system increases the second chamber sensing threshold to a third peak value. Then, the system decreases the second chamber sensing threshold with time from the third peak value toward a third steady-state value. The system decreases the second chamber sensing threshold in discrete steps from the third peak value toward the third steady-state value. The second peak value of the first chamber sensing threshold is approximately ⅜ of the first peak value of the first chamber sensing threshold.

Another aspect of the system provides, among other things, a method of detecting electrical first chamber and second chamber heart activity signals associated with respective first and second heart chambers. The system detects a first chamber depolarization indicated by the first chamber heart activity signal. The first chamber depolarization exceeds a time-varying first chamber sensing threshold. In response to the first chamber depolarization, the system increases a time-varying first chamber sensing threshold to a first peak value. Then, the system decreases the first chamber sensing threshold with time from the first peak value toward a first steady-state value. The system detects a second chamber event indicated by the second chamber heart activity signal. In response to the second chamber event, the system increases the first chamber sensing threshold to a second peak value. The second peak value is between the first peak and first steady-state values. Then, the system decreases the first chamber sensing threshold with time from the second peak value toward a second steady-state value. The system adjusts the first peak value of the first chamber sensing threshold based at least in part on an amplitude of the detected first chamber depolarization. In one embodiment, these steps are repeated such that the system adjusts the first peak value of the first chamber sensing threshold based on a resulting plurality of first chamber depolarizations.

In various further embodiments, the system also increases, in response to the second chamber depolarization, the second chamber sensing threshold to a third peak value. Then, the system decreases the second chamber sensing threshold with time from the third peak value toward a third steady-state value. The system adjusts the third peak value of the second chamber sensing threshold based at least in part on an amplitude of the detected second chamber depolarization. In one embodiment, these steps are repeated such that: (1) the system adjusts the first peak value of the first chamber sensing threshold based on a resulting plurality of first chamber depolarizations, and (2) the system adjusts the third peak value of the second chamber sensing threshold based on a resulting plurality of second chamber depolarizations. In one embodiment, the second peak value of the first chamber sensing threshold is approximately ⅜ of the first peak value of the first chamber sensing threshold.

Another aspect of the system provides, among other things, a system for automatically adjusting a sensing threshold in a cardiac rhythm management device. The system includes a first chamber detector, which is electrically coupled to detect a first chamber event associated with a first chamber of a heart. A second chamber detector is electrically coupled to detect a second chamber event associated with a second chamber of the heart. A threshold controller includes a time-varying first chamber sensing threshold. The threshold controller is coupled to the first chamber detector. The first chamber sensing threshold increases, in response to the first chamber event, to a first peak value. The first chamber sensing threshold then decreases with time from the first peak value toward a first steady-state value. The threshold detector also is coupled to the second chamber detector. The first chamber sensing threshold increases, in response to the second chamber event, to a second peak value. This second peak value is between the first peak and first steady-state values. The first chamber sensing threshold then decreases with time from the second peak value toward a second steady-state value.

In various further embodiments, the first chamber event is a first chamber depolarization. The threshold controller includes a peak adjustment circuit that adjusts the first peak value of the first chamber sensing threshold based on a detected amplitude of the first chamber depolarization received from the first chamber detector. An automatic gain control (AGC) circuit is coupled to the first chamber detector. The AGC circuit adjusts a detected amplitude of the first chamber depolarization received from the first chamber detector. In one embodiment, the system further includes a first leadwire, adapted for coupling the first chamber detector to an area in or near the first chamber of the heart, and a second leadwire, adapted for coupling the second chamber detector to an area in or near the second chamber of the heart. The first heart chamber includes a portion of the heart associated with one of a right atrium, a right ventricle, a left atrium, or a left ventricle heart chambers, and the second heart chamber includes a portion of the heart that is associated with a different one of the above-listed heart chambers.

Another aspect of the system includes, among other things, a system for automatically adjusting a sensing threshold in a cardiac rhythm management device. The system includes a first chamber detector, which is electrically coupled to detect a first chamber event associated with a first chamber of a heart. A second chamber detector is electrically coupled to detect a second chamber event associated with a second chamber of the heart. A threshold controller includes a time-varying first chamber sensing threshold. The threshold controller is coupled to the first chamber detector. The first chamber sensing threshold increases, in response to the first chamber event, to a first peak value. The first chamber sensing threshold then decreases with time from the first peak value toward a first steady-state value. The threshold detector is also coupled to the second chamber detector. If the first chamber sensing threshold has decreased at the time of the second chamber event to approximately below a predetermined comparison value that is between the first peak and first steady-state values, then: (a) the first chamber sensing threshold increases in response to the second chamber event to a second peak value, which is between the first peak and first steady-state values, and (b) the first chamber sensing threshold then decreases with time from the second peak value toward a second steady-state value.

In various further embodiments, the first chamber event is a first chamber depolarization. The threshold controller includes a peak adjustment circuit that adjusts the first peak value of the first chamber sensing threshold based on a detected amplitude of the first chamber depolarization received from the first chamber detector. An automatic gain control (AGC) circuit is coupled to the first chamber detector. The AGC circuit adjusts a detected amplitude of the first chamber depolarization received from the first chamber detector. In a further embodiment, a first leadwire is adapted for coupling the first chamber detector to a portion of the heart associated with the first chamber of the heart. A second leadwire is adapted for coupling the second chamber detector to a portion of the heart associated with the second chamber of the heart.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method of detecting electrical first and second chamber heart activity signals associated with first and second chambers of a heart, respectively, the method comprising:

detecting a first chamber event indicated by the first chamber heart activity signal;

increasing, in response to the first chamber event, a time-varying first chamber sensing threshold to a first peak value, and then decreasing the first chamber sensing threshold with time from the first peak value toward a first steady-state value;

detecting a second chamber event indicated by the second chamber heart activity signal; and increasing, in response to the second chamber event, the first chamber sensing threshold to a second peak value, which is between the first peak and first steady-state values, and then decreasing the first chamber sensing threshold with time from the second peak value toward a second steady-state value.

2. The method of claim 1, in which detecting the first chamber event includes an action selected from the group consisting of:

detecting a first chamber depolarization that exceeds the first chamber sensing threshold; and detecting a first chamber pace pulse.

3. The method of claim 1, in which detecting the second chamber event includes detecting a second chamber depolarization that exceeds a second chamber sensing threshold.

4. The method of claim 3, in which the second chamber sensing threshold is time-varying.

5. The method of claim 1, in which detecting the second chamber event includes detecting a second chamber pace pulse.

6. The method of claim 1, in which detecting the first and second chamber events is selected from the group consisting of:

detecting the first chamber event associated with a right atrium and detecting the second chamber event associated with a right ventricle;

detecting the first chamber event associated with a right atrium and detecting the second chamber event associated with a left ventricle;

detecting the first chamber event associated with a right atrium and detecting the second chamber event associated with a left atrium;

detecting the first chamber event associated with a right ventricle and detecting the second chamber event associated with a right atrium;

detecting the first chamber event associated with a right ventricle and detecting the second chamber event associated with a left atrium;

detecting the first chamber event associated with a right ventricle and detecting the second chamber event associated with a left ventricle;

detecting the first chamber event associated with a left atrium and detecting the second chamber event associated with a left ventricle;

detecting the first chamber event associated with a left atrium and detecting the second chamber event associated with a right ventricle;

detecting the first chamber event associated with a left atrium and detecting the second chamber event associated with a right atrium;

detecting the first chamber event associated with a left ventricle and detecting the second chamber event associated with a left atrium;

detecting the first chamber event associated with a left ventricle and detecting the second chamber event associated with a right ventricle; and detecting the first chamber event associated with a left ventricle and detecting the second chamber event associated with a right atrium.

7. The method of claim 1, further comprising, in response to detecting the second chamber event, ignoring the first chamber heart activity signal for a time period of less than approximately 15 milliseconds before increasing the first chamber sensing threshold to the second peak value.

8. The method of claim 1, in which the first steady-state value of the first chamber sensing threshold is approximately equal to the second steady-state value of the first chamber sensing threshold.

9. The method of claim 1, in which the second peak value of the first chamber sensing threshold is approximately 3/8 of the first peak value of the first chamber sensing threshold.

10. The method of claim 1, in which the second peak value of the first chamber sensing threshold is approximately 3/8 of an AGC lower limit when the first peak value of the first chamber sensing threshold is less than or equal to the AGC lower limit.

11. A method of detecting electrical first chamber and second chamber heart activity signals associated with first and second chambers of a heart, respectively, the method comprising:

detecting a first chamber event indicated by the first chamber heart activity signal, wherein the first chamber event consists of one of a first chamber pace pulse or a first chamber depolarization that exceeds a time-varying first chamber sensing threshold;

increasing, in response to the first chamber event, the first chamber sensing threshold to a first peak value, and then decreasing the first chamber sensing threshold with time from the first peak value toward a first steady-state value;

detecting a second chamber event indicated by the second chamber heart activity signal, wherein the second chamber event consists of one of a second chamber pace pulse or a second chamber depolarization that exceeds a time-varying second chamber sensing threshold;

increasing, in response to the second chamber event, the first chamber sensing threshold to a second peak value, which is between the first peak and first steady-state values, and then decreasing the first chamber sensing threshold with time from the second peak value toward a second steady-state value; and increasing, in response to the second chamber event, the second chamber sensing threshold to a third peak value, and then decreasing the second chamber sensing threshold from the third peak value toward a third steady-state value.

12. The method of claim 11, in which decreasing the first chamber sensing threshold includes decreasing the first chamber sensing threshold in discrete steps from the first peak value toward the first steady-state value.

13. The method of claim 11, in which decreasing the second chamber sensing threshold includes decreasing the second chamber sensing threshold in discrete steps from the third peak value toward the third steady-state value.

14. The method of claim 11, in which the first steady-state value of the first chamber sensing threshold is approximately equal to the second steady-state value of the first chamber sensing threshold.

15. The method of claim 11, in which the first steady-state value of the first chamber sensing threshold is different from the third steady-state value of the second chamber sensing threshold.

16. The method of claim 11, in which the second peak value of the first chamber sensing threshold is approximately 3/8 of the first peak value of the first chamber sensing threshold.

17. The method of claim 11, in which the second peak value of the first chamber sensing threshold is approximately 3/8 of an AGC lower limit when the first peak value of the first chamber sensing threshold is less than or equal to the AGC lower limit.

18. The method of claim 11, in which detecting the first and second chamber events is selected from the group consisting of:

detecting the first chamber event associated with a right atrium and detecting the second chamber event associated with a right ventricle;

detecting the first chamber event associated with a right atrium and detecting the second chamber event associated with a left ventricle;

detecting the first chamber event associated with a right atrium and detecting the second chamber event associated with a left atrium;

detecting the first chamber event associated with a right ventricle and detecting the second chamber event associated with a right atrium;

detecting the first chamber event associated with a right ventricle and detecting the second chamber event associated with a left atrium;

detecting the first chamber event associated with a right ventricle and detecting the second chamber event associated with a left ventricle;

detecting the first chamber event associated with a left atrium and detecting the second chamber event associated with a left ventricle;

detecting the first chamber event associated with a left atrium and detecting the second chamber event associated with a right ventricle;

detecting the first chamber event associated with a left atrium and detecting the second chamber event associated with a right atrium;

detecting the first chamber event associated with a left ventricle and detecting the second chamber event associated with a left atrium;

detecting the first chamber event associated with a left ventricle and detecting the second chamber event associated with a right ventricle; and detecting the first chamber event associated with a left ventricle and detecting the second chamber event associated with a night atrium.

19. A method of detecting electrical first chamber and second chamber heart activity signals associated with a first and second chambers of a heart, respectively, the method comprising:

detecting a first chamber event indicated by the first chamber heart activity signal, wherein the first chamber event consists of one of a first chamber pace pulse or a first chamber depolarization that exceeds a time-varying first chamber sensing threshold;

increasing, in response to the first chamber event, the first chamber sensing threshold to a first peak value, and then decreasing the first chamber sensing threshold with time from the first peak value toward a first steady-state value;

detecting a second chamber event indicated by the second chamber heart activity signal, wherein the second chamber event consists of one of a second chamber pace pulse or a second chamber depolarization that exceeds a time-varying second chamber sensing threshold; and if the first chamber sensing threshold has decreased approximately below a predetermined comparison value, which is between the first peak and first steady-state values, then increasing, in response to the second chamber event, the first chamber sensing threshold to a second peak value, which is between the first peak and first steady-state values, and then decreasing the first chamber sensing threshold with time from the second peak value toward a second steady-state value.

20. The method of claim 19, in which the predetermined comparison value is approximately equivalent to the second peak value of the first chamber sensing threshold.

21. The method of claim 19, in which the first and second steady-state values of the first chamber sensing threshold are approximately equivalent.

22. The method of claim 19, in which decreasing the first chamber sensing threshold with time from the first peak value toward the first steady-state value includes decreasing the first chamber sensing threshold in discrete steps from the first peak value toward the first steady-state value.

23. The method of claim 19, further comprising increasing, in response to detecting the second chamber event, the second chamber sensing threshold to a third peak value, and then decreasing the second chamber sensing threshold with time from the third peak value toward a third steady-state value.

24. The method of claim 23, in which decreasing the second chamber sensing threshold includes decreasing the second chamber sensing threshold in discrete steps from the third peak value toward the third steady-state value.

25. The method of claim 19, in which the second peak value of the first chamber sensing threshold is approximately ⅜ of the first peak value of the first chamber sensing threshold.

26. A method of detecting electrical first chamber and second chamber heart activity signals associated with first and second chambers of a heart, respectively, the method comprising:

(A) detecting a first chamber depolarization indicated by the first chamber heart activity signal, wherein the first chamber depolarization exceeds a time-varying first chamber sensing threshold;

(B) increasing, in response to the first chamber depolarization, a time-varying first chamber sensing threshold to a first peak value, and then decreasing the first chamber sensing threshold with time from the first peak value toward a first steady-state value;

(C) detecting a second chamber event indicated by the second chamber heart activity signal;

(D) increasing, in response to the second chamber event, the first chamber sensing threshold to a second peak value, which is between the first peak and first steady-state values, and then decreasing the first chamber sensing threshold with time from the second peak value toward a second steady-state value; and (E) adjusting the first peak value of the first chamber sensing threshold based at least in part on an amplitude of the first chamber depolarization detected in (A).

27. The method of claim 26, in which (A)–(E) are repeated, and (E) includes adjusting the first peak value of the first chamber sensing threshold based on a plurality of first chamber depolarizations resulting from the repeating of (A).

28. The method of claim 26, in which the second chamber event of (C) is a second chamber depolarization that exceeds a time-varying second chamber sensing threshold, and further comprising:

(F) increasing, in response to the second chamber depolarization, the second chamber sensing threshold to a third peak value, and then decreasing the second chamber sensing threshold with time from the third peak value toward a third steady-state value; and (G) adjusting the third peak value of the second chamber sensing threshold based at least in part on an amplitude of the second chamber depolarization detected in (C).

29. The method of claim 28, in which (A)–(G) are repeated, and (E) includes adjusting the first peak value of the first chamber sensing threshold based on a plurality of first chamber depolarizations resulting from the repeating of (A), and (G) includes adjusting the third peak value of the second chamber sensing threshold based on a plurality of second chamber depolarizations resulting from the repeating of (G).

30. The method of claim 26, in which the second peak value of the first chamber sensing threshold is approximately ⅜ of the first peak value of the first chamber sensing threshold.

31. A system for automatically adjusting a sensing threshold in a cardiac rhythm management device, the system comprising:

a first chamber detector, electrically coupled to detect a first chamber event associated with a first chamber of a heart;

a second chamber detector, electrically coupled to detect a second chamber event associated with a second chamber of the heart; and a threshold controller, including a time-varying first chamber sensing threshold, the threshold controller being coupled to the first chamber detector, the first chamber sensing threshold increasing, in response to the first chamber event, to a first peak value, the first chamber sensing threshold then decreasing with time from the first peak value toward a first steady-state value, the threshold detector also being coupled to the second chamber detector, the first chamber sensing threshold increasing, in response to the second chamber event, to a second peak value, which is between the first peak and first steady-state values, the first chamber sensing threshold then decreasing with time from the second peak value toward a second steady-state value.

32. The system of claim 31, in which the first chamber event is a first chamber depolarization, and the threshold controller includes a peak adjustment circuit that adjusts the first peak value of the first chamber sensing threshold based on a detected amplitude of the first chamber depolarization received from the first chamber detector.

33. The system of claim 31, further comprising an automatic gain control (AGC) circuit, coupled to the first chamber detector, the AGC circuit adjusting a detected amplitude of the first chamber depolarization received from the first chamber detector.

34. The system of claim 31, further comprising:

a first leadwire, adapted for coupling the first chamber detector to the first chamber of the heart; and a second leadwire, adapted for coupling the second chamber detector to the second chamber of the heart.

35. The system of claim 31, in which the first and second chambers are selected from the group consisting of:

the first chamber including a right atrium and the second chamber including a right ventricle;

the first chamber including a right atrium the second chamber including a left ventricle;

the first chamber including a right atrium and the second chamber including a left atrium;

the first chamber including a right ventricle the second chamber including a right atrium;

the first chamber including a right ventricle and the second chamber including a left atrium;

the first chamber including a right ventricle and the second chamber including a left ventricle;

the first chamber including a left atrium and the second chamber including a left ventricle;

the first chamber including a left atrium and the second chamber including a right ventricle;

the first chamber including a left atrium and the second chamber including a right atrium;

the first chamber including a left ventricle and the second chamber including a left atrium;

the first chamber including a left ventricle and the second chamber including a right ventricle; and the first chamber including a left ventricle and the second chamber including a right atrium.

36. A system for automatically adjusting a sensing threshold in a cardiac rhythm management device, the system comprising:

a first chamber detector, electrically coupled to detect a first chamber event associated with a first chamber of a heart;

a second chamber detector, electrically coupled to detect a second chamber event associated with a second chamber of the heart; and a threshold controller, including a time-varying first chamber sensing threshold, the threshold controller being coupled to the first chamber detector, the first chamber sensing threshold increasing, in response to the first chamber event, to a first peak value, the first chamber sensing threshold then decreasing with time from the first peak value toward a first steady-state value, the threshold detector also being coupled to the second chamber detector, wherein if the first chamber sensing threshold has decreased at the time of the second chamber event to approximately below a predetermined comparison value that is between the first peak and first steady-state values, then: (a) the first chamber sensing threshold increases in response to the second chamber event to a second peak value, which is between the first peak and first steady-state values, and (b) the first chamber sensing threshold then decreases with time from the second peak value toward a second steady-state value.

37. The system of claim 36, in which the first chamber event is a first chamber depolarization, and the threshold controller includes a peak adjustment circuit that adjusts the first peak value of the first chamber sensing threshold based on a detected amplitude of the first chamber depolarization received from the first chamber detector.

38. The system of claim 36, further comprising an automatic gain control (AGC) circuit, coupled to the first chamber detector, the AGC circuit adjusting a detected amplitude of the first chamber depolarization received from the first chamber detector.

39. The system of claim 36, further comprising:

a first leadwire, adapted for coupling the first chamber detector to a portion of the heart that is associated with the first chamber of the heart; and a second leadwire, adapted for coupling the second chamber detector to a portion of the heart that is associated with the second chamber of the heart.

40. The system of claim 36, in which the first and second chambers are selected from the group consisting of:

the first chamber including a right atrium and the second chamber including a right ventricle;

the first chamber including a right atrium the second chamber including a left ventricle;

the first chamber including a right atrium and the second chamber including a left atrium;

the first chamber including a right ventricle the second chamber including a right atrium;

the first chamber including a right ventricle and the second chamber including a left atrium;

the first chamber including a right ventricle and the second chamber including a left ventricle;

the first chamber including a left atrium and the second chamber including a left ventricle;

the first chamber including a left atrium and the second chamber including a right ventricle;

the first chamber including a left atrium and the second chamber including a right atrium;

the first chamber including a left ventricle and the second chamber including a left atrium;

the first chamber including a left ventricle and the second chamber including a right ventricle; and the first chamber including a left ventricle and the second chamber including a right atrium.

* * * * *

UNITED STATES PATENT AND TRADEMARK OFFICE
CERTIFICATE OF CORRECTION

PATENT NO.: 6,169,918 B1
DATED: Jan. 2, 2001
INVENTOR(S) : Haefner et al.

It is certified that error appears in the above-identified patent and that said Letters Patent is hereby corrected as shown below:

In column 1, line 46, delete "an high" and insert --a high--, therefor.

In column 4, line 30, delete "operation a cardiac" and insert --operation of a cardiac--, therefor.

In column 10, line 65, delete "triggers in" and insert --triggers an--, therefor.

In column 11, line 49, delete "triggers in" and insert --triggers an--, therefor.

In column 11, line 59, delete "illustrated" and insert --illustrates--, therefor.

In column 19, line 53, insert --with time from the first peak value toward the first steady-state value-- after "threshold".

In column 20, line 51, delete "night" and insert --right--, therefor.

In column 22, line 27, delete "electrically coupled to detect" and insert --for detecting--, therefor.

In column 22, line 30, delete "electrically coupled to detect" and insert --for detecting--, therefor.

In column 22, line 32, delete "and" after "heart;".

In column 22, line 35, delete "detector," and insert --detector to control--, therefor.

In column 22, line 36, delete "increasing" and insert --to increase--, therefor.

In column 22, line 37, insert --and to control-- after "value,".

In column 22, line 38, delete "then decreasing" and insert --to decrease--, therefor.

UNITED STATES PATENT AND TRADEMARK OFFICE
CERTIFICATE OF CORRECTION

PATENT NO.: 6,169,918 B1
DATED: Jan. 2, 2001
INVENTOR(S) : Haefner et al.

It is certified that error appears in the above-identified patent and that said Letters Patent is hereby corrected as shown below:

In column 22, line 40, delete "value," and insert --value; and--, therefor.

In column 22, line 40, delete "detector" and insert --controller--, therefor.

In column 22, line 41, delete "detector," and insert --detector to control--, therefor.

In column 22, line 42, delete "increasing" and insert --to increase--, therefor.

In column 22, line 44, insert --and to control-- after "values,".

In column 22, line 45, delete "then decreasing" and insert --to decrease--, therefor.

In column 22, line 52, delete "a detected" and insert --an--, therefor.

In column 22, line 53, delete "received" and insert --detected--, therefor.

In column 22, line 56, delete "a detected" and insert --an--, therefor.

In column 22, line 57, delete "received" and insert --detected--, therefor.

In column 22, lines 65-66, delete "which the first and second chambers are selected" and insert --which the first and second lead wires are adapted for the first and second chambers selected--, therefor.

In column 23, line 28, delete "electrically coupled to detect" and insert --for detecting--, therefor.

In column 23, line 31, delete "electrically coupled to detect" and insert --for detecting--, therefor.

In column 23, line 33, delete "and" after "heart;".

UNITED STATES PATENT AND TRADEMARK OFFICE
CERTIFICATE OF CORRECTION

PATENT NO.: 6,169,918 B1

DATED: Jan. 2, 2001

INVENTOR(S) : Haefner et al.

It is certified that error appears in the above-identified patent and that said Letters Patent is hereby corrected as shown below:

In column 23, line 36, delete "detector," and insert --detector to control--, therefor.

In column 23, line 37, delete "increasing" and insert --to increase--, therefor.

In column 23, line 38, insert --and to control-- after "value,".

In column 23, line 39, delete "then decreasing" and insert --to decrease--, therefor.

In column 23, line 41, delete "value," and insert --value; and--, therefor.

In column 23, line 41, delete "detector" and insert --controller--, therefor.

In column 23, line 43, delete "the time" and insert --a time--, therefor.

In column 23, line 46, delete "then:" and insert --then the threshold controller controlling:--, therefor.

In column 23, line 47, delete "increases" and insert --to increase--, therefor.

In column 23, line 49, insert --controlling-- after "values, and".

In column 23, line 50, delete "then decreases" and insert --to decrease--, therefor.

In column 24, line 7, delete "a detected" and insert --an--, therefor.

In column 24, line 8, delete "received" and insert --detected--, therefor.

In column 24, line 11, delete "a detected" and insert --an--, therefor.

In column 24, line 12, delete "received" and insert --detected--, therefor.

UNITED STATES PATENT AND TRADEMARK OFFICE
CERTIFICATE OF CORRECTION

PATENT NO.: 6,169,918 B1
DATED: Jan. 2, 2001
INVENTOR(S): Haefner et al.

It is certified that error appears in the above-identified patent and that said Letters Patent is hereby corrected as shown below:

In column 24, lines 22-23, delete "which the first and second chambers are selected" and insert --which the first and second lead wires are adapted for the first and second chambers selected--, therefor.

Signed and Sealed this

Twenty-ninth Day of May, 2001

Attest:

NICHOLAS P. GODICI

Attesting Officer

Acting Director of the United States Patent and Trademark Office